(12) United States Patent
Hammerstone et al.

(10) Patent No.: US 8,268,373 B2
(45) Date of Patent: Sep. 18, 2012

(54) METHOD FOR EXTRACTING COCOA PROCYANIDINS

(75) Inventors: John F. Hammerstone, Rockville, MD (US); Mark J. Chimel, Gaithersburg, MD (US)

(73) Assignee: Mars, Incorporated, McLean, VA (US)

( * ) Notice: Subject to any disclaimer, the term of this patent is extended or adjusted under 35 U.S.C. 154(b) by 420 days.

(21) Appl. No.: 11/865,424

(22) Filed: Oct. 1, 2007

(65) Prior Publication Data

US 2008/0051587 A1    Feb. 28, 2008

Related U.S. Application Data

(62) Division of application No. 10/292,027, filed on Nov. 12, 2002, which is a division of application No. 09/590,931, filed on Jun. 9, 2000, now Pat. No. 6,627,232.

(51) Int. Cl.
*A23G 1/00* (2006.01)
*A61K 36/00* (2006.01)

(52) U.S. Cl. ............. 426/45; 424/776; 424/725; 426/44

(58) Field of Classification Search ........................ None
See application file for complete search history.

(56) References Cited

U.S. PATENT DOCUMENTS

| | | | |
|---|---|---|---|
| 1,855,026 A | 4/1932 | Livingston et al. | |
| 1,925,326 A | 9/1933 | Kellogg et al. | |
| 2,512,663 A | 6/1950 | Masurovsky | |
| 2,954,293 A * | 9/1960 | Rusoff | 426/417 |
| 4,156,030 A | 5/1979 | Eggen | |
| 4,237,288 A | 12/1980 | Rushmore | |
| 4,390,698 A | 6/1983 | Chiovini et al. | |
| 4,407,834 A | 10/1983 | Chiovini et al. | |
| 4,444,798 A | 4/1984 | Magnolato et al. | |
| 4,755,391 A | 7/1988 | Bigalli et al. | |
| 4,758,444 A | 7/1988 | Terauchi et al. | |
| 4,871,562 A | 10/1989 | Terauchi et al. | |
| 4,908,212 A | 3/1990 | Kwon et al. | |
| 5,338,554 A | 8/1994 | Vogt et al. | |
| 5,554,645 A | 9/1996 | Romanczyk, Jr. et al. | |
| 5,712,305 A | 1/1998 | Romanczyk, Jr. et al. | |
| 5,912,363 A | 6/1999 | Nafisi-Movaghar et al. | |
| 5,968,517 A | 10/1999 | Duncan et al. | |
| 6,015,913 A | 1/2000 | Kealey et al. | |

(Continued)

FOREIGN PATENT DOCUMENTS

AU    A-87879/98    4/1999

(Continued)

OTHER PUBLICATIONS

Intl. Search Report/PCT/US01/18963.

(Continued)

*Primary Examiner* — Patricia Leith
(74) *Attorney, Agent, or Firm* — Nath, Goldberg & Meyer; Sheldon M. McGee

(57) ABSTRACT

A cocoa extract which is rich in procyanidin monomer and oligomers is made by extracting de-fatted, unroasted, unfermented cocoa beans with organic solvents. The yield of procyanidins in an extract varies with the type of solvent used, reaction temperature, reaction pH and whether or not the solvent is an aqueous solution. Extraction parameters can be optimized to increase procyanidin yield, and different conditions results in the preferential extraction of the higher or lower oligomers. A preferred extraction method is countercurrent extraction method.

6 Claims, 23 Drawing Sheets

Graph showing the oligomeric profiles of a) an ethyl acetate extraction of cocoa solids and b) an acetone/water/HoAc extract of the ethyl acetate-extracted solids

U.S. PATENT DOCUMENTS

| | | | |
|---|---|---|---|
| 6,159,451 | A | 12/2000 | Kim et al. |
| 6,207,702 | B1 * | 3/2001 | Schmitz et al. ............... 514/453 |
| 6,576,275 | B1 | 6/2003 | Hoving et al. |
| 2002/0176916 | A1 | 11/2002 | Purtle et al. |
| 2003/0206981 | A1 | 11/2003 | Lee et al. |
| 2003/0211184 | A1 | 11/2003 | Hoving et al. |

FOREIGN PATENT DOCUMENTS

| | | |
|---|---|---|
| CA | 2249501 | 4/1999 |
| CN | 1092063 A | 9/1994 |
| EP | 0 348 781 | 1/1990 |
| GB | 2 011 239 | 7/1978 |
| JP | HEI 7-213251 | 8/1995 |
| JP | 7-274894 | 10/1995 |
| JP | 9-224606 | 9/1997 |
| JP | 9-234018 | 9/1997 |
| WO | WO 97/36597 | 10/1997 |
| WO | WO 99/45788 | 9/1999 |
| WO | WO 99/45797 | 9/1999 |
| WO | WO 00/45769 | 8/2000 |
| WO | WO 02/14251 | 2/2002 |

OTHER PUBLICATIONS

P. Bastide, "Change in and Metabolism of the Phenolic Compounds in Cocoa Beans during Their Development . . ." Jul. 1987.

Clapperton et al., Proceedings 16th International Conference of Groupe Polyphenols, Lisbon, Portugal 1992 pp. 112-115.

H. Fincke, "Handbook of Cocoa Products" (1965).

Forysthe, Biochem. J. 1955 60:108-111.

Forysthe, Biochem. J. 1960 74:374-378.

Griffiths, Biochem. J. 1960 74:362-365.

Karim et al., J. Nutr. 2000 130 (Suppl.85) 21055-21089.

Mahbubul et al., Phytochemistry, 1977, 16: 1377-1380.

Naito et al., Nippon Shokuhin Kogyo Gakkaishi, J. of Japan. Soc. of Food Sci and Technol. 1982 29(9): 530-533.

Osawa et al., 1st Int'l Symp. on Chocolate and Cocoa Nutrition, Tokyo, Japan Sep. 27, 1995, 14 pages, pp. 3, 7, 8 and 9 Only provided.

Paolino et al., Archs. Oral Biol. 1985 30 (4):359-363.

Porter et al., Phytochemistry 1991 30 (5): 1657-1663.

Porter, Chapter 2, The Flavanoids 1988 21-62.

Rigaud et al., J. Chromatog. 1993 654:255-260.

Ziegleder et al., CCB Rev. for Choc. Confect Bakery 1983 8:3-6.

"Study on the Process Technique of Green Tea Polyphenol Extraction", Journal of Anhui Inst. of Technology 1997 16(1):6-11 (Original Chinese and Translation).

A. Yanagide et al., J. Chromatog. A (2000) 890:251-259.

Osawa et al., 1st Int'l Symp. on Chocolate add Cocoa Nutrition, Tokyo, Japan Sep. 27, 1995 pp. 1 and 5-7.

* cited by examiner

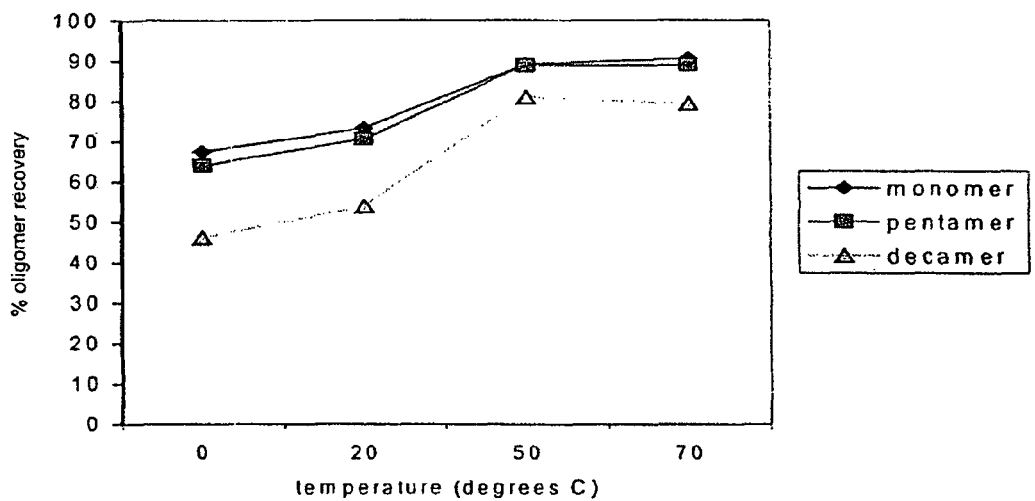
Figure 1a Effect of temperature on yield of monomers, pentamers and decamers using 100% ethanol as the extraction solvent
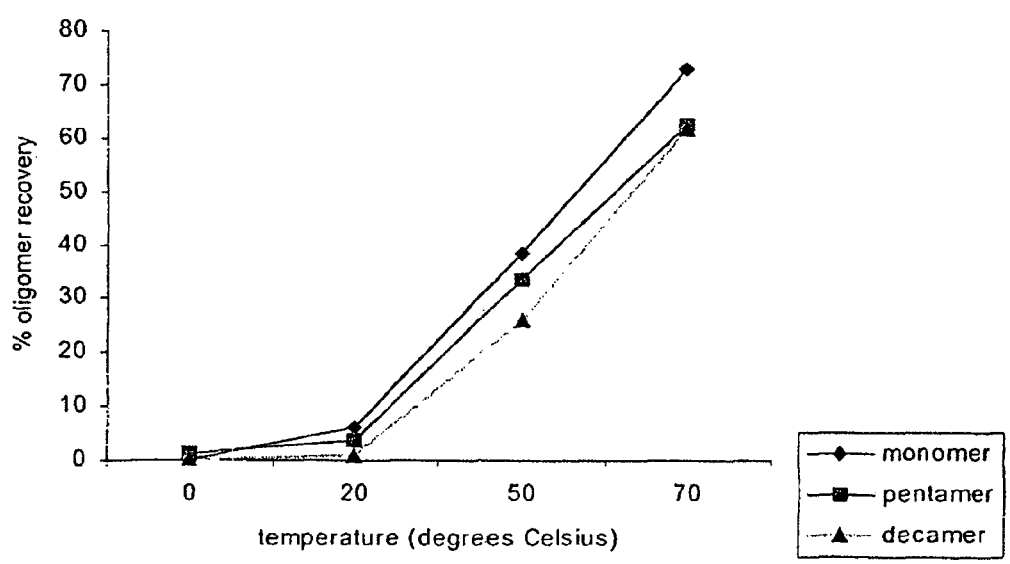
Figure 1b Effect of temperature on yield of monomers, pentamers and decamers using 100% isopropanol as the extraction solvent

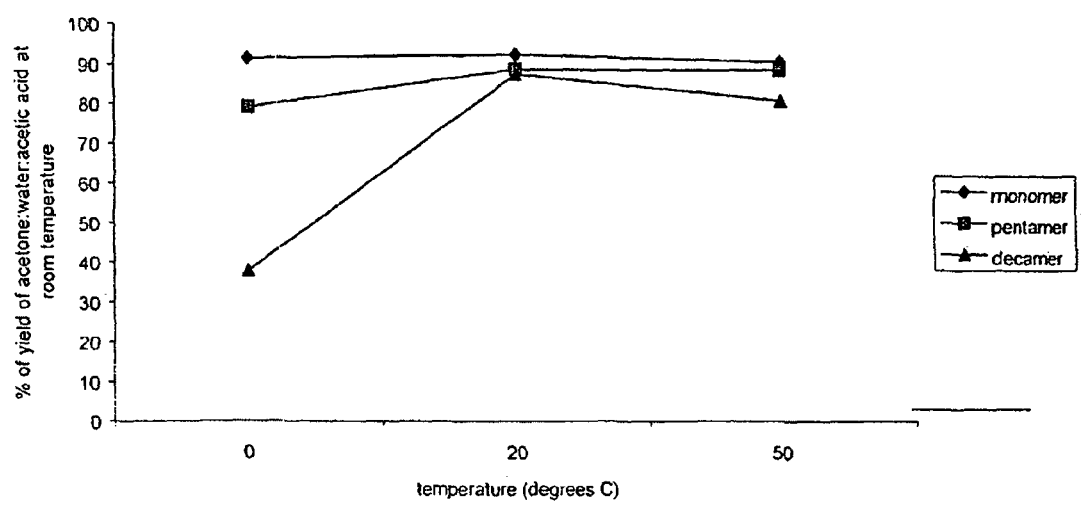
Figure 1c Effect of temperature on the yield of monomers, pentamers and decamers using 100% methanol as the solvent

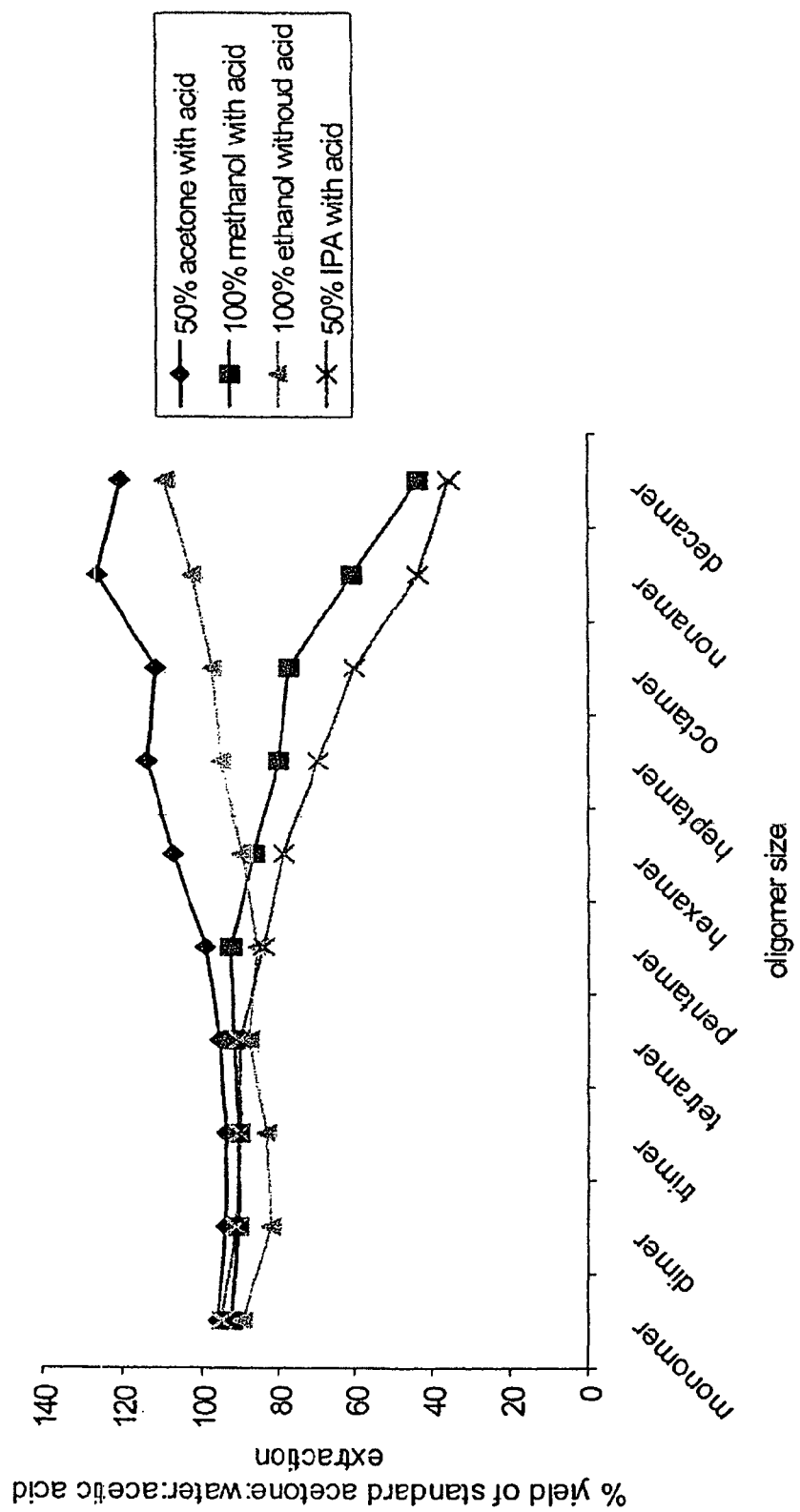
Figure 2 Graph showing that acetone and ethanol are most effective for extracting the higher oligomers at 50°C

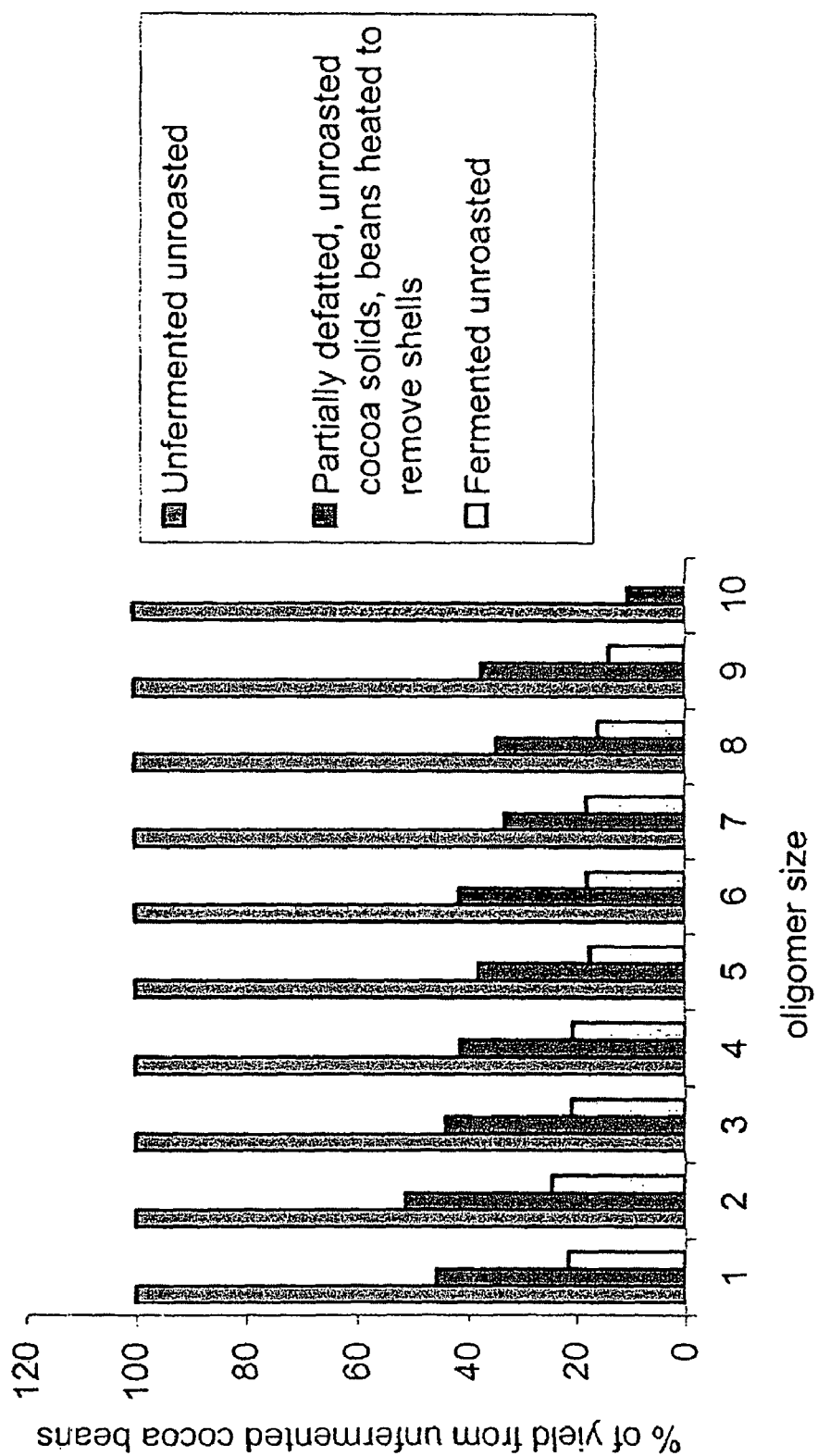

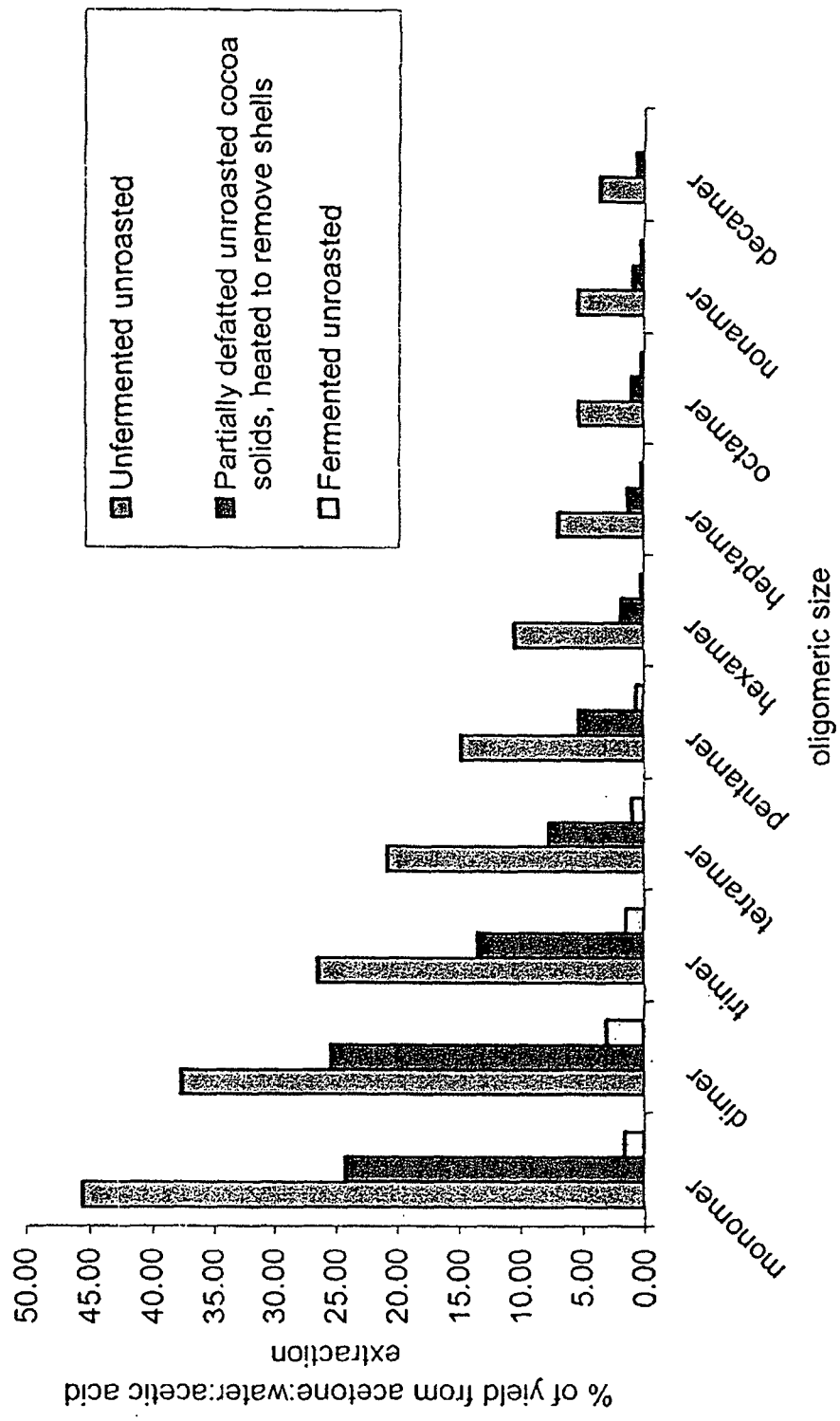
Figure 4 Graph showing the effect of fermentation and bean processing on extraction of procyanidins with boiling water

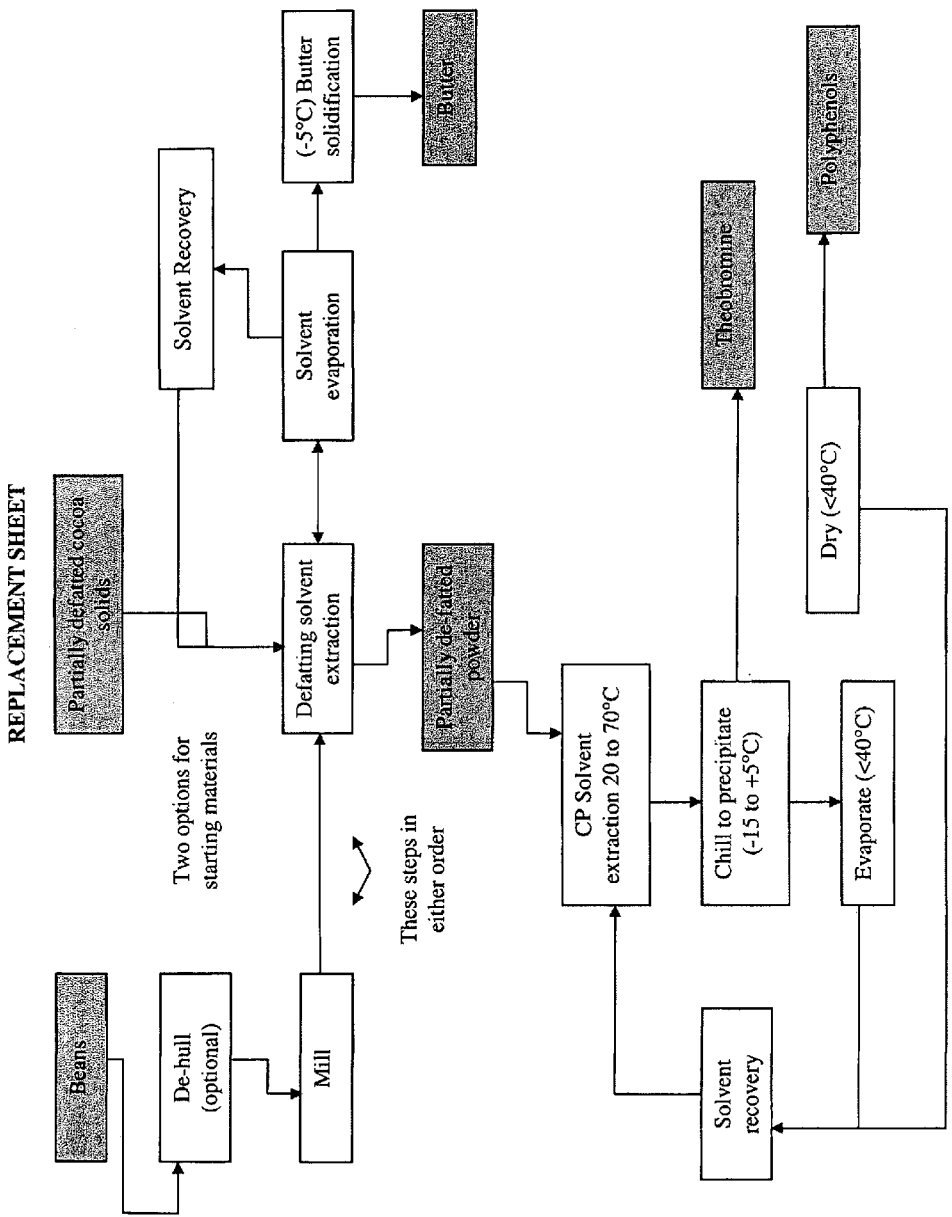
Figure 5 Cocoa Polyphenol Extract Process

Figure 7 Graph showing the oligomeric profiles of a) an ethyl acetate extraction of cocoa solids and b) an acetone/water/HoAc extract of the ethyl acetate-extracted solids

FIGURE 9

| % Isopropanol | monomer | dimer | trimer | tetramer | pentamer | hexamer | heptamer | octomer | nonamer | decamer |
|---|---|---|---|---|---|---|---|---|---|---|
| 50% | 94.92 | 91.17 | 90.37 | 90.53 | 84.23 | 78.98 | 69.86 | 60.42 | 43.83 | 35.76 |
| 60% | 97.26 | 93.03 | 91.17 | 89.46 | 80.58 | 72.75 | 59.97 | 50.09 | 35.11 | 26.49 |
| 70% | 94.96 | 90.52 | 86.12 | 78.97 | 64.32 | 50.80 | 35.59 | 25.53 | 14.56 | 8.60 |
| 80% | 94.70 | 86.16 | 73.96 | 57.96 | 38.61 | 24.02 | 12.71 | 6.66 | 0.00 | 0.00 |
| 100% | 58.45 | 50.89 | 50.12 | 49.49 | 46.67 | 44.33 | 40.38 | 38.49 | 34.85 | 29.12 |

Figure 9. Average Percentage Recovery Using Isopropanol or Aqueous Isopropanol 0.5% Acid at 50°C

FIGURE 10

| % Isopropanol | monomer | dimer | trimer | tetramer | pentamer | hexamer | heptamer | octomer | nonamer | decamer |
|---|---|---|---|---|---|---|---|---|---|---|
| 50% | 93.25 | 88.96 | 86.61 | 84.58 | 82.82 | 75.01 | 66.54 | 60.77 | 50.05 | 18.18 |
| 60% | 92.59 | 87.90 | 84.57 | 80.67 | 79.46 | 63.73 | 55.08 | 48.00 | 36.44 | 9.09 |
| 70% | 93.32 | 90.43 | 83.09 | 73.31 | 65.00 | 45.45 | 30.11 | 24.13 | 14.15 | 1.52 |
| 80% | 40.52 | 35.71 | 25.75 | 20.38 | 17.77 | 14.16 | 11.93 | 11.73 | 8.88 | 1.61 |
| 100% | 42.14 | 38.95 | 37.56 | 36.24 | 35.81 | 32.10 | 32.05 | 30.75 | 28.22 | 22.14 |

Figure 10. Average Percentage Recovery Using Isopropanol or Aqueous Isopropanol without Acid at 50°C

FIGURE 11

| % Methanol | monomer | dimer | trimer | tetramer | pentamer | hexamer | heptamer | octomer | nonamer | decamer |
|---|---|---|---|---|---|---|---|---|---|---|
| 50% | 86.98 | 85.48 | 80.24 | 74.98 | 72.26 | 58.27 | 55.21 | 50.00 | 39.88 | 0.00 |
| 60% | 91.60 | 89.66 | 85.22 | 81.26 | 77.00 | 66.19 | 56.50 | 48.93 | 31.90 | 0.00 |
| 70% | 92.46 | 95.23 | 95.57 | 97.15 | 90.90 | 84.33 | 72.67 | 60.82 | 41.82 | 28.95 |
| 80% | 88.53 | 94.10 | 92.86 | 92.43 | 85.80 | 78.57 | 66.00 | 54.12 | 36.36 | 21.05 |
| 100% | 92.40 | 90.73 | 90.76 | 92.06 | 92.82 | 86.94 | 80.34 | 77.63 | 61.13 | 43.86 |

Figure 11. Average Percentage Recovery Using Methanol or Aqueous Methanol with 0.5% Acid at 50°C

FIGURE 12

| % Methanol | monomer | dimer | trimer | tetramer | pentamer | hexamer | heptamer | octomer | nonamer | decamer |
|---|---|---|---|---|---|---|---|---|---|---|
| 50% | 79.50 | 74.32 | 69.48 | 63.73 | 56.62 | 46.92 | 35.86 | 28.09 | 17.02 | 8.33 |
| 60% | 81.04 | 76.33 | 72.66 | 67.65 | 62.15 | 52.56 | 39.80 | 32.58 | 20.21 | 12.50 |
| 70% | 87.07 | 82.60 | 76.19 | 39.18 | 60.85 | 51.18 | 42.18 | 36.71 | 35.48 | 18.75 |
| 80% | 89.49 | 84.94 | 77.82 | 70.78 | 62.09 | 52.35 | 42.18 | 34.18 | 29.03 | 12.50 |
| 100% | 84.94 | 76.41 | 77.73 | 78.06 | 76.62 | 76.41 | 69.74 | 71.91 | 62.77 | 66.67 |

Figure 12. Average Percentage Recovery Using Methanol without Acid at 50°C

FIGURE 13

| % Methanol | monomer | dimer | trimer | tetramer | pentamer | hexamer | heptamer | octomer | nonamer | decamer |
|---|---|---|---|---|---|---|---|---|---|---|
| 50% | 95.93 | 93.96 | 93.97 | 95.69 | 99.64 | 107.73 | 114.39 | 112.33 | 126.81 | 121.05 |
| 60% | 95.28 | 94.81 | 94.84 | 95.78 | 97.65 | 100.78 | 104.29 | 103.62 | 111.35 | 111.40 |
| 80% | 97.14 | 95.21 | 95.56 | 94.08 | 92.57 | 91.95 | 94.11 | 76.32 | 82.86 | 66.91 |
| 100% | 77.30 | 73.43 | 74.55 | 77.56 | 76.03 | 74.05 | 63.03 | 54.02 | 13.04 | 13.16 |

Figure 13. Average Percentage Recovery Using Acetone with 0.5% Acid at 50°C

FIGURE 14

| % Methanol | monomer | dimer | trimer | tetramer | pentamer | hexamer | heptamer | octomer | nonamer | decamer |
|---|---|---|---|---|---|---|---|---|---|---|
| 50% | 89.36 | 84.69 | 86.20 | 85.61 | 86.67 | 94.77 | 94.17 | 108.94 | 108.21 | 140.59 |
| 60% | 98.18 | 115.95 | 75.54 | 98.67 | 100.16 | 102.95 | 102.95 | 105.39 | 100.94 | 131.95 |
| 80% | 103.54 | 103.34 | 102.89 | 100.64 | 94.97 | 93.21 | 80.23 | 80.56 | 68.05 | 24.42 |
| 100% | 72.07 | 68.20 | 69.57 | 73.20 | 73.88 | 78.36 | 71.70 | 68.66 | 0.00 | 0.00 |

Figure 14. Average Percentage Recovery Using Acetone without Acid at 50°C

FIGURE 15

| % Methanol | monomer | dimer | trimer | tetramer | pentamer | hexamer | heptamer | octomer | nonamer | decamer |
|---|---|---|---|---|---|---|---|---|---|---|
| 50% | 86.02 | 83.17 | 80.77 | 79.85 | 77.00 | 69.94 | 66.73 | 52.21 | 37.80 | 19.09 |
| 60% | 88.12 | 84.02 | 81.00 | 77.88 | 75.92 | 68.33 | 61.83 | 44.00 | 32.21 | 15.76 |
| 70% | 87.97 | 82.66 | 78.61 | 74.24 | 68.21 | 58.39 | 48.77 | 32.99 | 18.87 | 3.33 |
| 80% | 91.49 | 82.90 | 75.51 | 67.29 | 57.72 | 45.53 | 36.21 | 24.08 | 13.34 | 0.00 |
| 100% | 81.48 | 75.53 | 75.15 | 75.76 | 76.69 | 76.10 | 78.53 | 71.12 | 68.92 | 63.03 |

Figure 15. Average Percentage Recovery Using Ethanol with 0.5% Acid at 50°C

FIGURE 16

| % Ethanol | monomer | dimer | trimer | tetramer | pentamer | hexamer | heptamer | octomer | nonamer | decamer |
|---|---|---|---|---|---|---|---|---|---|---|
| 50% | 84.43 | 82.32 | 79.33 | 78.40 | 76.55 | 67.21 | 53.33 | 39.88 | 29.07 | 3.33 |
| 60% | 87.99 | 86.04 | 82.58 | 81.69 | 78.17 | 66.74 | 51.11 | 36.90 | 23.26 | 6.67 |
| 70% | 87.96 | 83.40 | 78.00 | 74.01 | 67.99 | 55.58 | 41.11 | 28.57 | 17.44 | 6.67 |
| 80% | 91.85 | 86.62 | 83.11 | 81.00 | 71.02 | 63.13 | 53.08 | 43.75 | 37.36 | 18.33 |
| 100% | 89.44 | 81.87 | 83.24 | 87.94 | 85.76 | 90.00 | 95.29 | 97.75 | 102.91 | 109.86 |

Figure 16. Average Percentage Recovery Using Ethanol without 0.5% Acid at 50°C

FIGURE 17

| °C | monomer | dimer | trimer | tetramer | pentamer | hexamer | heptamer | octomer | nonamer | decamer |
|---|---|---|---|---|---|---|---|---|---|---|
| 0 | 2.44 | 1.94 | 1.71 | 1.47 | 1.12 | 0.88 | 0.68 | 0.46 | 0.00 | 0.00 |
| 20 | 5.85 | 4.97 | 4.54 | 4.11 | 3.55 | 3.06 | 2.63 | 2.39 | 0.93 | 1.03 |
| 50 | 38.21 | 36.43 | 36.04 | 35.27 | 33.57 | 31.62 | 30.56 | 30.44 | 25.27 | 25.89 |
| 70 | 72.76 | 69.92 | 68.99 | 65.75 | 62.41 | 59.30 | 57.32 | 60.45 | 54.34 | 61.33 |

Figure 17. Effect of Temperature on Percentage of Cocoa Procyanidin Monomers and Oligomers Extracted using 100% Isopropanol

FIGURE 18

| °C | monomer | dimer | trimer | tetramer | pentamer | hexamer | heptamer | octomer | nonamer | decamer |
|---|---|---|---|---|---|---|---|---|---|---|
| 0 | 91.22 | 89.43 | 85.98 | 83.10 | 79.01 | 76.36 | 69.78 | 68.47 | 58.15 | 37.72 |
| 20 | 92.20 | 95.87 | 93.65 | 92.94 | 88.56 | 91.54 | 87.13 | 81.94 | 84.38 | 87.35 |
| 50 | 90.47 | 92.41 | 91.91 | 90.22 | 88.33 | 87.46 | 86.85 | 88.67 | 82.52 | 80.69 |

Figure 18. Effect of Temperature on Percentage of Cocoa Procyanidin Monomers and Oligomers Extracted using 100% Methanol

FIGURE 19

| °C | monomer | dimer | trimer | tetramer | pentamer | hexamer | heptamer | octomer | nonamer | decamer |
|---|---|---|---|---|---|---|---|---|---|---|
| 0 | 67.66 | 68.17 | 67.84 | 67.49 | 63.93 | 62.28 | 58.98 | 53.72 | 46.69 | 46.06 |
| 20 | 73.27 | 72.88 | 73.03 | 72.90 | 70.61 | 69.83 | 64.53 | 63.43 | 59.68 | 53.85 |
| 50 | 89.12 | 88.22 | 89.39 | 91.22 | 88.84 | 86.35 | 86.26 | 86.87 | 73.57 | 80.90 |
| 70 | 90.52 | 88.21 | 89.17 | 91.32 | 88.97 | 87.93 | 87.06 | 87.06 | 82.82 | 79.31 |

Figure 19. Effect of Temperature on Percentage of Cocoa Procyanidin Monomers and Oligomers Extracted using 100% Ethanol

FIGURE 20

| | monomer | dimer | trimer | tetramer | pentamer | hexamer | heptamer | octomer | nonamer | decamer |
|---|---|---|---|---|---|---|---|---|---|---|
| Acetone/water/acetic acid extract from unfermented beans | 100 | 100 | 100 | 100 | 100 | 100 | 100 | 100 | 100 | 100 |
| Ethyl acetate extract from unfermented beans | 47.77 | 34.94 | 25.77 | 17.63 | 9.98 | 5.28 | 3.43 | 0 | 0 | 0 |
| Acetone/water/acetic acid extract of ethyl acetate-extracted cocoa solids | 66.47 | 72.81 | 78.5 | 83.45 | 89.05 | 92.96 | 96.08 | 97.87 | 100 | 100 |

Figure 20. Comparison of Oligomeric Yields Obtained by Dual Extraction With Ethyl Acetate followed by Acetone/Water/Acetic Acid

FIGURE 21

| Solvents/Temp. | Theobromine mg/g | Caffeine mg/g |
|---|---|---|
| isopropanol @ | 0 | 0 |
| isopropanol @ 20°C | Trace | Trace |
| isopropanol @ 50°C | 1.7 | Trace |
| isopropanol @ 70°C | 3.5 | 0.15 |
| methanol @ 0°C | 1.17 | Trace |
| methanol @ 20°C | 1.56 | 0.16 |
| methanol @ 50°C | 1.88 | 0.19 |
| ethanol @ 0°C | 1.16 | Trace |
| ethanol @ 20°C | 3.58 | 0.16 |
| ethanol @ 50°C | 4.45 | 0.18 |
| ethanol @ 70°C | 3.73 | 0.16 |

Figure 21. Yields of Caffeine and Theobromine Extracted from Cocoa Beans using Various Solvents at Various Temperatures

FIGURE 22

| | monomer | dimer | trimer | tetramer | pentamer | hexamer | heptamer | octomer | nonamer | decamer |
|---|---|---|---|---|---|---|---|---|---|---|
| powder from unfermented beans | 93.27 | 105.99 | 99.58 | 95.26 | 81.02 | 64.44 | 46.03 | 30 | 18.8 | 12.5 |
| powder from fermented beans | 64 | 56.41 | 50 | 36.84 | 33.33 | 33.33 | 0 | 0 | 0 | 0 |

Figure 22. Comparison of Oligomeric Yields from Extracts Obtained from Fermented and Unfermented Cocoa Beans using 80% Ethanol at 80°C

METHOD FOR EXTRACTING COCOA PROCYANIDINS

This application is a division of Ser. No. 10/292,027 filed Nov. 12, 2002, now pending, which is a division of Ser. No. 09/590,931 filed Jun. 9, 2000, now U.S. Pat. No. 6,627,232 issued Sep. 30, 2003.

FIELD OF THE INVENTION

This invention is directed to improved methods for the extraction of cocoa procyanidin monomers and oligomers from the cocoa solids.

It is known that the regulation consumption of dietary polyphenols, commonly found in a variety of fruits and vegetables, is beneficial. Red wine, green tea and cocoa have all been identified as being rich in polyphenols, and the regular consumption of red wine and green tea have both been shown to be inversely associated with heart disease deaths in industrialized countries.

BACKGROUND OF THE INVENTION

It is well-known that the polyphenols of cocoa contribute significantly to the development of flavour in the fermented and roasted cocoa bean. Astringent and bitter flavors in cocoa have been traditionally associated with the presence of xanthine alkaloids and polyphenols in the cocoa beans. For this reason, various methods have been developed over the years to extract the cocoa polyphenols to verify their presence, to quantify their amounts, and to identify them. The cocoa polyphenols are primarily cocoa procyanidins. However, no extraction method has thus far been optimized to yield extracts high in cocoa procyanidins.

It is now known that the cocoa procyanidin oligomers show a clear relationship between structure and function, meaning that individual oligomers, or fractions containing several oligomers of a similar size, show specific biological functions which are not affected by other oligomers. Thus, it is important to ensure that the extraction procedure utilized not only results in the highest possible solubilization of the cocoa polyphenols, but that it is effective at extracting all the cocoa polyphenol oligomers present in the bean.

The extraction of cocoa beans using water or an organic solvent, or a mixture of water and an organic solvent has been used to remove the xanthine alkaloids (predominantly caffeine and theobromine) and other soluble constituents of the cocoa bean which impart a bitter, disagreeable flavor. Included among these bitter-tasting soluble constituents are the procyanidins.

U.S. Pat. No. 1,750,795 (issued to Defren in 1926) discloses a process for removing the "greater part of the soluble bitter constituents of the beans" by soaking the beans in water at 60° C. and then discarding the water and roasting the beans.

Hot water treatments have been used to remove the xanthines in order to provide stimulant-free cocoa beans. See U.S. Pat. No. 4,407,834 "Detheobromination of Cocoa" (issued to Chiovini et al., Jun. 28, 1983) and U.S. Pat. No. 4,755,391 "Removal of Methylxanthines from Cacao Materials" (issued to Bigalli et al., Jul. 5, 1988).

Cocoa extracts have been prepared by extracting cocoa solids, prepared from fermented, conventionally roasted cocoa beans or cocoa nibs, with water and/or alcohols. Osakabe et al. used ethanol, either absolute or aqueous at greater than 40% v/v with deionized water at ambient temperature to prepare a crude polyphenol extract. See JP 946-64717 "Food or Beverage Product for Preventing Gastric Ulcers" (Oct. 4, 1995).

Zieglader et al. used methanol to extract the polyphenols from cocoa beans at ambient temperature. See "Antioxidative Effects of Cocoa" (Rev. Choc. Confect. Bank, 8:3-6, 1983) which discloses the preparation of a methanol extract. The extract contained "monomer tannin precursors (catechins, anthocyanidins and their soluble condensates)" and that is used as an additive for oil to preserve it from oxidation. Griffiths et al. used methanol extracts, again obtained at ambient temperatures, to obtain polyphenol extracts from ripe cocoa nibs which were used to study the characterization of plant polyphenols in cocoa and other plants. See "A Comparative Study of the Seed Polyphenols of the Genus *Theobroma*", (Biochemical J. 74:362-365, 1960). Rigaud et al. made an extract from lyophilized cocoa beans and grape seeds and noted that the use of methanol as a solvent precluded the presence of the higher oligomers. See "Normal-Phase High-Performance Liquid Chromatographic Separation of Procyanidins from Cacao Beans and Grape Seeds (J. Chromatography 654:255-60, 1993). Jalal & Collin prepared extracts from different parts of the cocoa plant in order to analyze the polyphenols present in each part of the plant. The extraction was carried out using 70% cold methanol, followed by ethyl acetate. See Polyphenols of Mature Plant, Seedling and Tissue Cultures of *Theobroma Cacao*" (Phytochemistry, 16:1377-1380, 1977).

Acetone/water has also been used for cocoa bean extractions. Clapperton et al. report the extraction of defatted cocoa powder made from fermented cocoa bens using cold 70% acetone. See "Polyphenols and Cocoa Flavor, Groupe Polyphenols," (XVI$^{th}$ Intern. Conf., Lisbon, Portugal, Jul. 13-16, 1992). Rigaud combines a first extraction with ethanol with a second extraction using a 60% acetone/water mixture. See "Normal-Phase High-Performance Liquid Chromatographic Separation of Procyanidins from Cacao Beans and Grape Seeds" (J. Chromatography 654:255-60, 1993).

Traditionally, cocoa beans are treated and processed in such a way as to minimize the bitter taste which the polyphenols impart to the beans, and this results in a reduction of the polyphenol content of the bean. The two ways in which the polyphenol content is significantly reduced are fermentation of cocoa beans in their husks and roasting the fermented cocoa beans in order to crack their husks and aid in the de-hulling process. Zieglader et al. report a loss of antioxidant activities in extracts from cocoa beans which are fermented compared to extracts from unfermented beans and correlate this reduction in antioxidant potential with a reduced amount of polyphenols in the extracts of fermented beans. All the previously discussed extraction methods were carried out using fermented beans, and in many cases the beans were also roasted. Therefore, the procyanidin yields are much lower than those found in extracts from unfermented beans.

It has been a common practice to follow an initial solvent extraction step with an ethyl acetate extraction step. See Forsyth & Roberts, "Cacao Polyphenolic Substances: 3. The Structure of Cacao Leucocyanidin 1" Biochem. J. 74 374-378, 1960; Thompson et al., "Plant Procyanidins. Part 1. Introduction: the Isolation, Structure and Distribution in Nature of Plant Procyanidins", J. Chem. Soc. Perkin 1, Vol. 11, 1387-99, 1972; Jalal & Colllins, "Polyphenols of Mature Plant, Seedling and Tissue Cultures of *Theobroma Cacao*", Phytochemistry, 16:1377-1380, 1977; Porter et al. "Flavans and Proanthocyanidins" Chapter Two in "The Flavanoids", Ed., J.B. Harborne, Chapman and Hall Ltd., London, 1988; and U.S. Pat. No. 5,554,645 (issued Oct. 3, 1994 to Romanczyk et al). This has the effect of producing an extract which contains the monomers and lower oligomers and none, or very little, of the higher oligomers. See Lea A. "The Phenolics of Ciders: Oligomeric and Polymeric Procyanidins", J. Sci. Fd. Agric. 29 471-477, 1978.

Whether or not the cocoa beans are defatted prior to extraction has an impact upon the yield of polyphenols extracted. If the beans are not defatted, the fat in the beans interferes with the solubilizing activity of the solvent, and the polyphenol yields are considerably reduced (Lazarus et al. "Flavonoids and Other Polyphenols" in Methods in Enzymology series. Edited by Lester Packer, Academic Press, New York, in press).

Cocoa extracts have been prepared from cocoa solids prepared from unfermented or fermented sun dried cocoa beans. The beans were ground, defatted and extracted. A 70% acetone/30% deionized water mixture was used, followed by a 70% methanol extraction and two chloroform extractions. Then follows an extraction with ethyl acetate, the addition of water, and the removal of the ethyl acetate. Alternatively, the beans were extracted with 70% acetone. In both cases the extractions were carried out at room temperature and the aqueous extracts were freeze-dried. See U.S. Pat. No. 5,554,645 (issued Oct. 3, 1994 to L. Romanczyk et al.).

Furthermore, cocoa extracts can be prepared from partially defatted cocoa solids that are prepared from cocoa beans which have not been roasted. The resulting cocoa solids, whether prepared from fermented, underfermented, or unfermented cocoa nibs, have a higher cocoa polyphenol content, i.e., cocoa procyanidin content, than cocoa solids prepared from conventionally roasted cocoa beans or cocoa nibs. See U.S. Pat. No. 6,015,913 (issued Jan. 18, 2000 to K. S. Kealey et al.).

Defatted, freeze-dried, unfermented cocoa beans contain about 2% xanthine alkaloids, and traditionally processed beans contain larger amounts. Theobromine is a degradation product of caffeine, and both are well-known stimulants of the nervous system. Excessive xanthine alkaloid intake is not thought to be beneficial. Hence, in some cases, it may be desirable to prepare cocoa extracts free of the xanthine alkaloids.

Thus, there is a need for an improved process to extract cocoa procyanidins from cocoa solids, and, in some cases, to decaffeinate and detheobrominate the cocoa extracts.

SUMMARY OF THE INVENTION

The present invention provides an improved method for extracting cocoa polyphenols including cocoa procyanidins from partially or fully defatted cocoa solids prepared from non-roasted cocoa beans. The improved process comprises a single extraction, at atmospheric pressure or under pressure, with a solvent selected from the group consisting of an acidified organic solvent capable of solubilizing the polyphenols, or aqueous mixtures thereof. An edible acid is added to solvent or aqueous-solvent mixture in an amount sufficient to lower the pH from about 6.5 to about 2 to about 4. The cocoa solids are prepared from unfermented or underfermented cocoa beans. The organic solvent may be selected from the group consisting of lower alkyl alcohols, lower alkyl ketones, and lower alkyl acetate. Suitable solvents include methanol, ethanol, isopropanol, acetone, methyl acetate, or ethyl acetate. The aqueous solvent mixture preferably contains up to about 50% water by volume. Preferred aqueous-solvent mixtures include isopropanol and about 50-70% water and isopropanol and about 20% water which preferentially extract monomers and oligomers up to and including hexamers, acetone and about 80% to about 100% water, acetone and about 50% to about 70% water, or 100% ethanol which preferentially extracts cocoa procyanidin oligomers higher than the heptamers.

The present invention also provides a method of extracting cocoa polyphenols including cocoa procyanidin monomers and oligomers from partially defatted or fully defatted cocoa solids prepared from cocoa beans that have not been roasted. The method comprises the step of extracting, at atmospheric pressure or under pressure, the cocoa solids with a non-acidified organic solvent capable of solubilizing cocoa polyphenols or non-acidified aqueous mixtures thereof. Preferably, the cocoa beans are unfermented or underfermented cocoa beans. The beans typically have a fermentation factor of 275 or less. The preferred beans include slaty, purple, or purple brown cocoa beans, or mixtures of slaty and purple cocoa beans, purple and brown cocoa beans, or slaty, purple and brown cocoa beans. The unfermented or underfermented cocoa beans contain at least about 1% up to about 15% by weight of total cocoa procyanidins per grain of defatted cocoa solids, typically about 4-7%. The organic solvent may be selected from the group consisting of a lower alkyl alcohol, a lower alkyl ketone, and a lower alkyl acetate. Suitable organic solvents are methanol, ethanol, isopropanol, acetone, methyl acetate, or ethyl acetate. The aqueous mixture can contain up to about 50% water by volume. Preferred solvents include 50-60% acetone, and 100% ethanol. The extraction can be carried out at a temperature from 0° C. up to the boiling point of the solvent or aqueous solvent mixture used at the extraction pressure used. When the solvent is methanol, the extraction is preferably carried out at room temperature. When the solvent is ethanol, the extraction is preferably carried out at about 20° C. to about 50° C. When the solvent is isopropanol, the extraction is preferably carried out at about 70° C. When the solvent is an aqueous-acetone mixture, the extraction is preferably carried out at about 50° C. up to the boiling point of the mixture.

In the above process, when an acidified solvent or solvent mixture is used, a lower extraction temperature is preferred. When a non-acidified solvent or solvent mixture is used, a higher extraction temperature can be used.

The present invention also provides a method for selectively extracting low molecular weight cocoa procyanidin oligomers from partially or fully defatted cocoa solids, prepared from cocoa beans that have not been roasted. The solvent used is a solvent which preferentially extracts the lower oligomers, e.g., methyl acetate or ethyl acetate. Preferably, the cocoa beans are unfermented or underfermented cocoa beans. The extraction is preferably carried out at about 20° C. to about 50° C. The resulting cocoa extracts consist essentially of monomers, dimers and trimers, The present invention also provides a method for selectively extracting higher molecular weight cocoa procyanidin oligomers from partially defatted or fully defatted cocoa solids prepared from coca beans that have not been roasted. The method comprises the steps of (a) extracting the cocoa solids with ethyl acetate; (b) recovering the extracted cocoa solids; (c) extracting the recovered extracted cocoa solids with a solvent which is a good solvent for the higher oligomer, e.g., acetone and ethanol and mixtures there up with up to 50% water; (d) separating the cocoa solids from the cocoa extract; and (e) optionally drying the cocoa extract. The extraction is preferably carried out at about 20° C. to about 50° C. Preferably the cocoa beans are unfermented or underfermented. The cocoa extracts consist essentially of at least tetramers and higher oligomers.

The present invention further provides a continuous method for extracting, at atmospheric pressure or under pressure, cocoa polyphenols including cocoa procyanidins from partially defatted or fully defatted cocoa solids using an organic solvent suitable for solubilizing cocoa procyanidins, or mixtures thereof with water. The process comprises the steps of (a) contacting a series of cells containing the cocoa solids with a solvent flowing in a counter-current direction, (b) recovering the cocoa extract, and (c) drying the cocoa extract. Preferred solvents include lower alkyl alcohols, lower alkyl ketones, and lower alkyl acetates. Suitable lower alkyl alcohols are methanol, ethanol, and isopropanol. A suitable lower alkyl ketones is acetone. Suitable lower alkyl acetates are methyl acetate and ethyl acetate. Preferably, the cocoa extract is recycled until substantially no more cocoa procyanidins are extracted from the cocoa solids. When the solvent is the organic solvent, the cocoa extract is dried by flashing off the solvent. When the solvent is the aqueous-organic mixture, the cocoa extract is dried by flashing off the solvent before drying the aqueous extract. The aqueous extracts can be dried by freeze drying, spray drying, flash drying, or drum drying.

The present invention provides a method for recovering cocoa procyanidins and theobromine from partially defatted or fully defatted cocoa solids, prepared from cocoa beans. The process comprises the steps of (a) extracting the cocoa solids with ethanol at about 50° C. to about 70° C., (b) chilling the ethanol extract at a temperature and for a time sufficient to precipitate out of the theobromine, (c) separating the precipitated out theobromine, and (d) removing the ethanol from extract to recover the dried cocoa procyanidins. Preferably, the beans are unfermented or underfermented cocoa beans that have not been roasted. The present invention also provides a method of minimizing the amount of theobromine in the cocoa procyanidins extracted from partially defatted or fully defatted cocoa solids, prepared from unroasted, preferably unfermented or underfermented, cocoa beans. The method comprises the steps of (a) extracting the cocoa solids with isopropanol to produce an alcoholic extract containing cocoa procyanidins and theobromine, (b) chilling the alcoholic extract at a temperature and for a time sufficient to precipitate out the theobromine, and (c) separating the theobromine from the alcoholic extract. In the above processes, the chilling is carried out by for up to about 12 hours at 0° C. to about 5° C. and the separating step is carried out by filtering the extract, the centrifuging the extract, or by absorbing the theobromine on a suitable absorbent.

DESCRIPTION OF THE DRAWINGS

FIG. 1(a) Graph showing the effect of temperature on yield of the monomer, pentamer and decamer using 100% ethanol as the extraction solvent.

FIG. 1(b) Graph showing the effect of temperature on yield of the monomer, pentamer and decamer using 100% isopropanol as the extraction solvent.

FIG. 1(c) Graph showing the effect of temperature on yield of the monomer, pentamer and decamer using 100% methanol as the extraction solvent.

FIG. 2 Graph showing that acetone and ethanol are most effective in extracting the higher oligomers.

FIG. 3 Graph showing the effects of fermentation and processing on procyanidin yields using an acetone:water acetic acid solvent as the standard.

FIG. 4 Graph showing the effect of fermentation and processing on procyanidin extraction with boiling water.

FIG. 5. A schematic diagram of the process of extracting polyphenols from cocoa beans.

FIG. 9 A table showing the average percentage recovery of monomer and oligomers (dimer through decamer) following extraction at 50° C. with isopropanol or aqueous isopropanol containing 0.5% acetic acid.

FIG. 10 A table showing the average percentage recovery of monomer and oligomers (dimer through decamer) following extraction at 50° C. with isopropanol or aqueous isopropanol containing no acid.

FIG. 11 A table showing the average percentage recovery of monomer and oligomers (dimer through decamer) following extraction at 50° C. with methanol or aqueous methanol containing 0.5% acetic acid.

FIG. 12 A table showing the average percentage recovery of monomer and oligomers (dimer through decamer) following extraction at 50° C. with methanol or aqueous methanol containing no acid.

FIG. 13 A table showing the average percentage recovery of monomer and oligomers (dimer through decamer) following extraction at 50° C. with acetone containing 0.5% acetic acid.

FIG. 14 A table showing the average percentage recovery of monomer and oligomers (dimer through decamer) following extraction at 50° C. with acetone containing no acid.

FIG. 15 A table showing the average percentage recovery of monomer and oligomers (dimer through decamer) following extraction at 50° C. with ethanol containing 0.5% acid.

FIG. 16 A table showing the average percentage recovery of monomer and oligomers (dimer through decamer) following extraction at 50° C. with ethanol containing no acid.

FIG. 17 A table which shows the effect of temperature on the percentage of monomer and oligomers extracted using 100% isopropanol.

FIG. 18 A table which shows the effect of temperature on the percentage of monomer and oligomers extracted using 100% methanol.

FIG. 19 A table which shows the effect of temperature on the percentage of monomer and oligomers extracted using 100% ethanol.

FIG. 20 A table which compares the yields of monomer and oligomers (dimer through decamer) obtained by a dual extraction of cocoa solids with ethyl acetate followed by aqueous acetone containing acetic acid.

FIG. 21 A table which shows the yields of caffeine and theobromine extracted from cocoa beans with isopropanol, methanol, and ethanol at various temperatures.

FIG. 22 A table which compares the yield of monomer and oligomers (dimer through decamer) in cocoa extracts obtained from fermented and unfermented cocoa beans by extraction with 80% ethanol at 80° C.

DETAILED DESCRIPTION OF THE INVENTION

Figure 6:
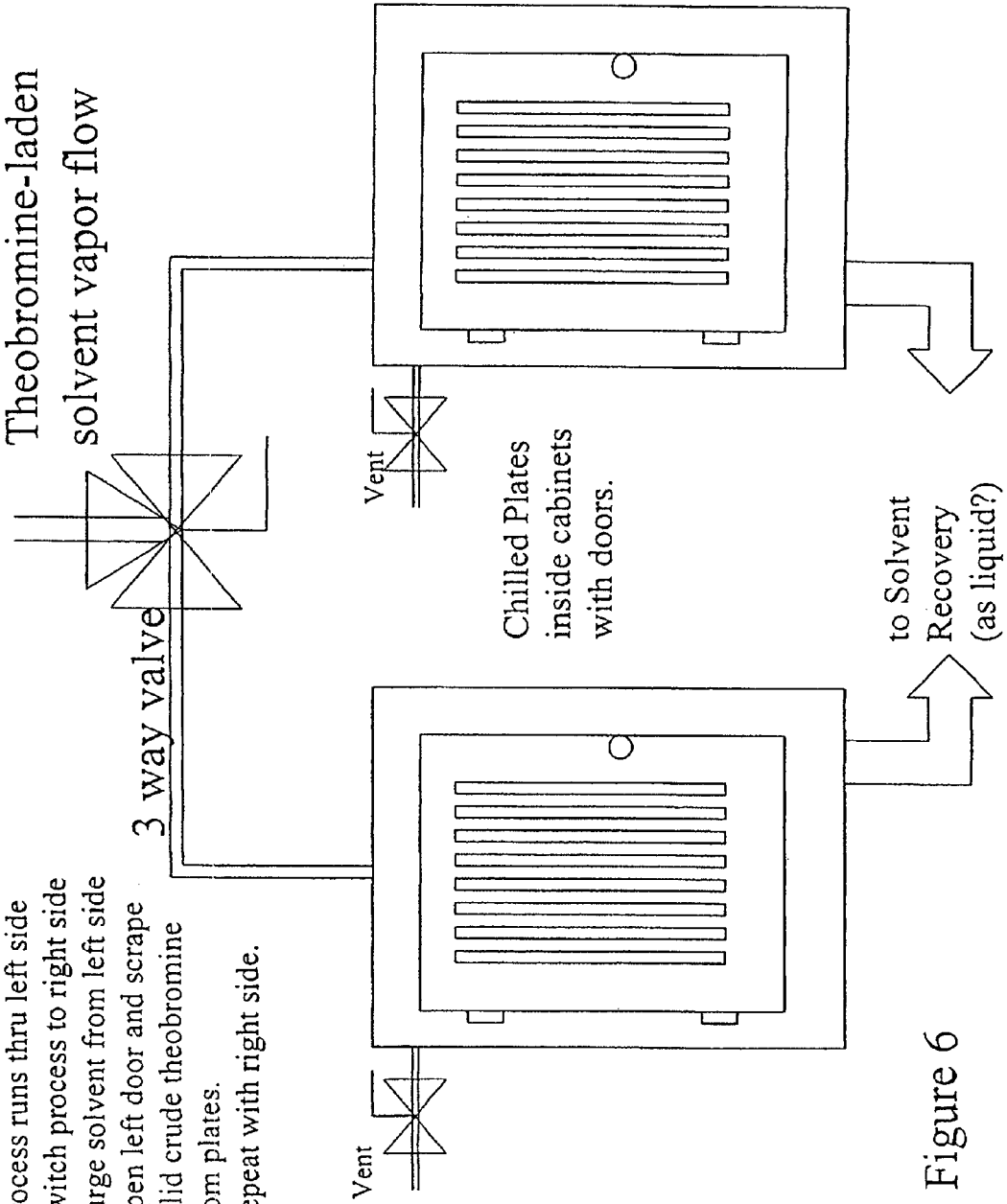
FIG. 6 A schematic diagram showing the process of de-theobrominating a cocoa extract.

Cocoa procyanidins can be obtained from several *Theobroma cacao* genotypes by the procedures discussed hereinafter. The procyanidin monomers include (+)-epicatechin), (−)-epicatechin and their respective epimers (i.e., (−)-catechin and (+)-epicatechin). The oligomers which have been identified in cocoa extracts include the dimers through the octadecamers. Cocoa procyanidins can also be obtained by synthetic methods described in PCT/US98/21392 (published as WO 99/19319 on Apr. 22, 1999) which is incorporated herein by reference. The oligomers may be linear or branched. The linear 4→8 oligomers have the structure:

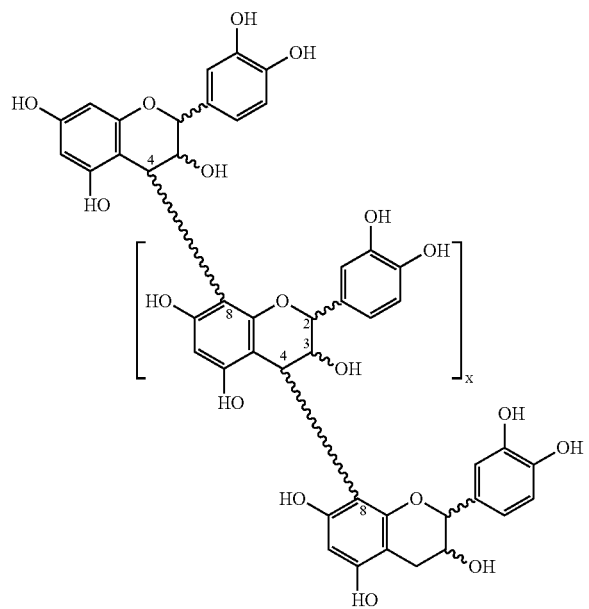

where x is an integer from 0-16.

The branched oligomers have the structure:

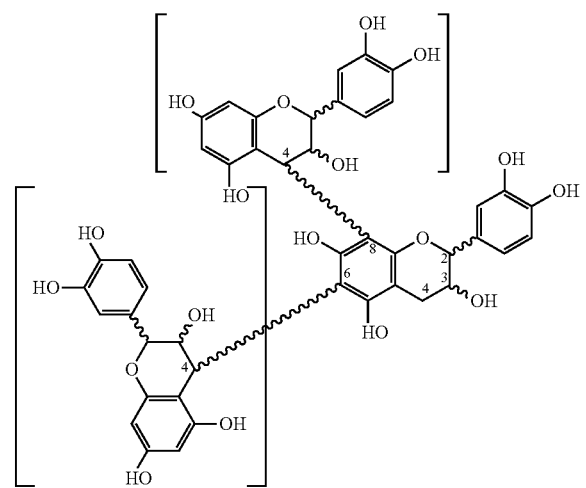

where a and b are independently integers from 0-15.

Structural variations to procyanidin oligomers may also occur with the formation of a second interflavonoid bond by carbon-oxygen oxidative coupling to form A-type oligomers, as shown below (Porter et al. "Flavans and Proanthocyanidins" Chapter Two in "The Flavonoids", Ed., J. B. Harborne, Chapman and Hall Ltd., London, 1988; Porter In Methods in Plant Biochemistry, Vol. I. Plant Phenolics. Dey and Harborne, Eds; Academic Press: San Diego, Calif., 1989). Due to the complexity of this conversion, A-type proanthocyanidins are not as frequently encountered as the single-bonded oligomers:

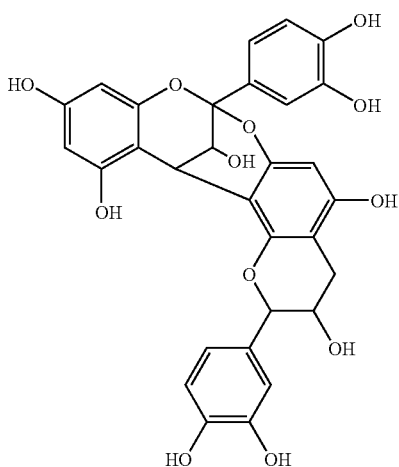

Cocoa beans can be divided into four categories based on their color: predominately brown (fully fermented), purple/brown, purple, and slaty (unfermented). Preferably, the cocoa solids used for extraction of the cocoa procyanidins are prepared from underfermented cocoa beans i.e., slaty cocoa beans, purple cocoa beans, mixtures of slaty and purple cocoa beans, mixtures of purple and brown cocoa beans, or mixture of slaty, purple, and brown cocoa beans. More preferably, the cocoa beans are slaty and/or purple. Unfermented cocoa beans have a higher cocoa polyphenol content than fermented beans (Kim and Keeney J. Food Sci. 49 1090, 1984; Porter et al., "Cacao Procyanidins: Major Flavonoids and Identification of Some Minor Metabolites" Phytochemistry, Vol. 30, No. 5, 1657-1663, 1991).

The cocoa polyphenol content of cocoa beans or blends thereof is higher when the beans have a fermentation factor of 275 or less. The "fermentation factor" is determined using a grading system for characterizing the fermentation of the cocoa beans. For example, slaty beans are designated 1, purple beans as 2, purple/brown beans as 3, and brown beans as 4. The percentage of beans falling within each category is multiplied by the weighted number. Thus, the "fermentation factor" for a sample of 100% brown beans would be 100×4 or 400, whereas for a 100% sample of purple beans it would be 100×2 or 200. A sample of 50% slaty beans and 50% purple beans would have a fermentation factor of 150[(50×1)+(50×2)].

Preferably, the unfermented or underfermented cocoa beans will contain at least 1% by weight of total cocoa procyanidins based on the weight of the nonfat cocoa solids, preferably 3-7% by weight, more preferably 7-12% by weight, and most preferably 13-15%.

A method for preparing a cocoa mass suitable for extraction is described in U.S. Pat. No. 5,554,645 (issued Sep. 10, 1996 to Romanczyk et al.), the disclosure of which is herein incorporated by reference Harvested cocoa pods were opened and the beans with pulp were removed for freeze-drying. The pulp was manually removed from the freeze-dried mass and the beans were subjected to the following manipulations. The freeze-dried cocoa beans were first manually dehulled and ground to a fine powdery mass with a TEXMAR Mill. The resultant mass was then defatted overnight by Soxhlet extraction using redistilled hexane as the solvent. Residual solvent was removed from the defatted mass by vacuum at ambient temperature.

Alternatively, the cocoa beans are sun dried under conditions which retard fermentation and the beans can be mechanically dried and then dehulled.

Partially defatted or nonfat cocoa solids having a higher cocoa polyphenol content, i.e., a high cocoa procyanidin content, can be obtained by processing the cocoa bean or cocoa nib without the roasting step and then milling the beans to chocolate liquor and recovering the partially defatted cocoa solids, or by screw pressing the roasted beans or nibs to partially defatted cocoa solids without a milling step. Even higher levels can be achieved if underfermented cocoa beans are used in this process. This method conserves the cocoa polyphenols because it omits the traditional roasting step. The method consists essentially of the steps of: (a) heating the cocoa beans to an internal bean temperature just sufficient to reduce the moisture content to about 3% by weight and loosen the cocoa shell, typically using a infra red heating apparatus for about 3 to 4 minutes; (b) winnowing the cocoa nibs from the cocoa shells; (c) screw pressing the cocoa nibs; and (d) recovering the cocoa butter and partially defatted cocoa solids which contain cocoa polyphenols including cocoa procyanidins. Optionally, the cocoa beans are cleaned prior to the heating step, e.g., in an air fluidized bed density separator. Preferably, the cocoa beans are heated to an internal bean temperature of about 100° C. to about 110° C., more preferably less than about 105° C. The winnowing can be carried out in an air fluidized bed density separator. The above process of heating the cocoa beans to reduce the moisture content and loosen the cocoa shell is disclosed in U.S. Pat. No. 6,015,913 (issued Jan. 18, 2000 to Kirk Kealey) which is herein incorporated by reference.

The internal bean temperature (IBT) can be measured by filling an insulated container such as a thermos bottle with beans (approximately 80-100 beans). In order to maintain the temperature of the beans during transfer from the heating apparatus to the thermos, the insulated container is then appropriately sealed in order to maintain the temperature of the sample therein. A thermometer is inserted into the bean filled insulated container and the temperature of the thermometer is equilibrated with respect to the beans in the thermos. The temperature reading is the IBT temperature of the beans. IBT can also be considered the equilibrium mass temperature of the beans.

In the context of this application, the following definitions apply. As used herein, higher oligomers include the hexamers to the decamers or higher and lower oligomers refer to procyanidins from the dimers up to and including the pentamers. As used herein, a cocoa extract is an extract containing an unspecified mixture of compounds which are extracted from ground cocoa beans, preferably dehulled beans, by slurrying defatted cocoa solids with an organic solvent and/or water and removing the cocoa solids to yield a liquid. The liquid extract can be dried by conventional methods known to those skilled in the art.

The extraction process comprises the steps of slurring the partially defatted or nonfat cocoa solids with an appropriate solvent or aqueous solvent-water mixture to solubilize the cocoa polyphenols, centrifuging the slurry to separate the extracted cocoa solids from the solvent phase, and removing the solvent(s). Preferably, the extraction process is a continuous process.

The solvent used can be any food grade organic solvent which will solubilize the cocoa procyanidin monomers and oligomers present in the cocoa solids. Preferably, the solvent is chosen from the group, consisting of lower alcohols such as methanol, ethanol, and isopropanol or ethyl acetate and acetone. The solvents can be used in aqueous solution or undiluted. Surprisingly, preferable dilutions vary with solvent used.

Acidification of the solvent mixture to a pH of about 2 to about 4 can either improve or reduce the efficiency of the procyanidin extraction depending upon the solvent used in the extraction procedure. The acid used in the reaction can be any food-grade, non-mineral acid. Preferred acids include formic acid, citric acid, phosphoric acid and, most preferably, acetic acid. Acids are not preferred if the extraction is carried out at a higher temperature.

The cocoa extracts can be detheobrominated and decaffeinated and the methylxanthines can be recovered and purified. The preferred solvent differs according to whether or not the methylxanthine is to be discarded or recovered. If it is to be discarded, the ideal extraction solvent is isopropanol at a low temperature. However, if the methylxanthine is to be recovered for purification, the ideal solvent is ethanol and the extraction should be carried out at between 50-70° C. The optimum conditions for methylxanthine removal must be balanced against the optimum conditions for procyanidin extraction to provide an effective simple process for the production of a methyl xanthine-free cocoa polyphenol extract.

The solvent extraction of the defatted cocoa solids can be carried out using either a batch process or a continuous counter-current process. In the batch process a large solvent to solids ratio is required to extract the procyanidins from the cocoa solids. Additionally, several consecutive washes are usually required to extract all of the available procyanidins. The preferred method of extraction is a continuous counter-current extraction. In this process the efficiency of extraction and the cost-effectiveness of the process is optimized, allowing it to be scaled up for manufacturing purposes. Use of a continuous counter-current flow of solvent through the cocoa solids allows the solvent to solids ratio to be much lower since the solvent can be continuously recycled. Additionally, due to the continuous flow of the solvent through the cocoa solids, it is not necessary to perform dual solvent extractions or to wash the solids with an aqueous solvent to ensure that all the procyanidins are extracted from the cocoa solids.

As will be shown hereafter, the efficacy of the procyanidin extraction varies significantly depending upon which solvent is used. Furthermore, it has been surprisingly found that while some solvents will preferentially extract the higher oligomers, other solvents will preferentially extract the monomers and lower oligomers. The type of solvent used, whether or not the solvent is an aqueous solution, the temperature at which the extraction is carried out, and other factors can affect the selective extraction of high or low molecular weight procyanidin oligomers. By sequentially carrying out the extraction of the same cocoa powder with two separate solvent systems, one known to extract monomer and the lower oligomers, and the other known to extract the higher oligomers, it is possible to obtain separate procyanidin fractions from the same extraction procedure, without following the extraction with complicated separation methods. Thus, a further embodiment of the invention is a process by which oligomers can be selectively extracted from cocoa solids in a large-scale, single step process which avoids the costly and complex process of chromatographically separating the oligomers.

Test Procedures

Control Extract

In the examples which follow all solvent extractions were compared to control extracts which were prepared by extracting unfermented, freeze-dried, defatted, cocoa beans prepared using the procedures described in Part A of Example 1. The solvent used was a mixture of 70% acetone, 29.5% water, and 0.5% acetic acid. All aqueous solutions are expressed as % (v/v). Ten grams of defatted cocoa mass was slurried with 100/mL of this solvent mixture and sonicated for 5-10 min. at 50° C. The slurry was centrifuged for 15 min. at 4° C. at 3000×G and the supernatant was passed through glass wool. The yields of crude procyanidins ranged from 15-20%.

Separation and Quantification of the Procyanidin Oligomers

Present in the Cocoa Extracts

In the examples which follow, the analytical methods described below were used to separate and quantify, by degree of polymerization, the procyanidin composition of the cocoa extracts. The method, described below, of identifying procyanidin oligomers in the cocoa extract is based upon work reported in Hammerstone, J. F. et al., "Identification of Procyanidins in Cocoa (*Theobroma cacao*) and Chocolate Using High-Performance Liquid Chromatography/Mass Spectrometry", *J. Ag. Food Chem.*; 1999; 47 (10) 490-496. The analytical methods described below were used in a qualitative study of a broad range of food and beverage samples reported to contain various types of proanthocyanidins, as reported in Lazarus, S. A., et al. "High-performance Liquid Chromatography/Mass Spectrometry Analysis of Proanthocyanidins in Foods and Beverages", *J. Ag. Food Chem.*; 1999; 47 (9); 3693-3701. The method of Lazarus et al. (1999) reported analysis using fluorescence detection because of higher selectivity and sensitivity.

The samples were analyzed using the analytical method reported in Adamson, G. E. et al., "HPLC Method for the Quantification of Procyanidins in Cocoa and Chocolate Samples and Correlation to Total Antioxidant Capacity", *J. Ag. Food Chem.*; 1999; 47 (10) 4184-4188. Samples were then compared directly to the control extract to accurately determine the levels of procyanidins monomers and oligomers in comparison to the monomers and oligomers in the control extract.

The total amount of procyanidins in an extract can also be determined using the method reported in Adamson et al. However, instead of comparing sample procyanidin levels with those of the control extract, the samples are compared with composite standard stock solutions of each of the monomers and oligomers, allowing the absolute amount of each procyanidin present in the extract to be calculated. Composite standard stock solutions and calibration curves were generated for the cocoa procyanidin monomers and oligomers by the method reported in Adamson et al.

EXAMPLES

Example 1

Cocoa Source and Preparation of Cocoa Powder Containing Cocoa Polyphenols

Part A—Preparation from Freeze-Dried Cocoa Beans

Methods for preparing a defatted cocoa mass are described in U.S. Pat. No. 5,554,645 (issued to Romanczyk Sep. 10, 1996) which is herein incorporated by reference. Unless otherwise stated, the cocoa beans used were unfermented and were processed in the following manner. Harvested cocoa pods were opened and the beans with pulp were removed for freeze-drying. The pulp was manually removed from the freeze-dried mass and the beans were subjected to the following manipulations. The freeze-dried cocoa beans were first manually dehulled and ground to a fine powdery mass with a TEKMAR Mill. The resultant mass was then defatted overnight by Soxhlet extraction using redistilled hexane as the solvent. Residual solvent was removed from the defatted mass by vacuum at ambient temperature.

Part B—Preparation From Roasted Cocoa Beans

The cocoa powder was prepared by a conventional method which comprises the steps of roasting the cocoa beans to an internal bean temperature of 95° C. to 160° C., winnowing the cocoa nibs from the roasted cocoa beans, milling the roasted cocoa nibs into chocolate liquor, pressing the liquor to extract the cocoa butter, and recovering the cocoa butter and partially defatted cocoa solids. The cocoa solids can be further defatted using hexane as a solvent, as previously described.

Part C—Preparation from Non-Roasted Cocoa Beans

Partially defatted cocoa solids having a high cocoa polyphenol content, i.e., a high cocoa procyanidin content, were obtained by processing the sun-dried, unfermented cocoa beans to cocoa solids without a bean or nib roasting step and, if desired, without the step of milling the beans to chocolate liquor, i.e., the beans can be screw pressed to provide cocoa butter and partially defatted cocoa solids. The cocoa polyphenols were conserved because the traditional roasting step was omitted. The method includes the steps of: (a) heating the cocoa beans to an internal bean temperature just sufficient to reduce the moisture content to about 3% by weight and loosen the cocoa shell; b) winnowing the cocoa nibs from the cocoa shells; (c) screw pressing the cocoa nibs; and (d) recovering the cocoa butter and partially defatted cocoa solids which contain cocoa polyphenols including cocoa procyanidins. Typically, the heating is carried out in an infra red heating apparatus for about 3 to 4 minutes. Optionally, the cocoa beans are cleaned prior to the heating step, e.g., in an air fluidized bed density separator. Preferably, the cocoa beans were heated to an internal bean temperature of about 100° C. to about 110° C., more preferably less than about 105° C. The winnowing can be earned out in an air fluidized bed density separator. The above process of heating the cocoa beans to reduce the moisture content and loosen the cocoa shell is disclosed in U.S. Pat. No. 6,015,913 (issued Jan. 18$^{th}$, 2000) which is herein incorporated by reference.

Example 2

Improved Extraction Processes

In the following series of experiments, the solvents and conditions used for the extractions were varied and compared in order to assess the efficiency of the different extraction processes. In addition to comparing the efficacy of various solvents, the effects of varying the extraction temperature, pH, and the ratio of water to solvent used were also compared.

Part A—Effect of Solvents at 50° C.

Extracts were prepared using cocoa solids prepared from unfermented, freeze-dried, defatted, cocoa beans as described in Part A of Example 1. Ten grams of the defatted cocoa mass were slurried with 100 mL of a solvent for 5-10 min. at 50° C. The solvents used were ethanol, methanol, isopropanol, and acetone. The solvent to water percentage was varied between 50-100%. The slurry was centrifuged for 5 min. at ambient temperature C at 3000×G and the supernatant passed through a 0.45 micron filter. The amount of procyanidins extracted and the oligomeric profile of the cocoa extract were determined using the analytical methods described above. The quantity of each oligomer detected was expressed as a percentage of the amount of the same oligomer extracted using the control extract described above.

Part B—Effect of pH

The effect of the addition of 0.5% acetic acid to the solvents was also studied. The extractions were carried out at temperatures of 0-70° C. These results are shown in FIGS. 15 and 16. Surprisingly, the presence or absence of 0.5% acetic acid in the solvent or aqueous solvent mixture had a variable effect on the extraction efficacy depending on the solvent being used and the solvent concentration.

Isopropanol and Isopropanol/Water

As can be seen from a comparison of the data in FIGS. 9 and 10, for isopropanol (IPA), the addition of acid resulted in an overall increase in oligomeric extraction at all solvent dilutions. However, the effect of adding acid to the 80% isopropanol doubled the amount of lower oligomers extracted, while leaving the amount of higher oligomers extracted largely unaltered.

Methanol and Methanol/Water

The addition of acid to the aqueous methanol solvents resulted in an increase in oligomeric yield. The 100% methanol, however, was unaffected by the presence of acid. This data is shown in FIGS. 11 and 12.

Acetone and Acetone/Water

The addition of acid to the acetone enhanced the extraction of monomers and dimers through heptamers, but had no effect on the extraction of the higher oligomers. The results are shown in FIGS. 13 and 14.

Ethanol and Ethanol/Water

The addition of acid to the aqueous ethanol solvents had very little effect on the extraction of monomers and oligomers up to the heptamers, but it enhanced the extraction of the higher oligomers. The extraction of the heptamers and higher oligomers was significantly more effective when there was no acid present in the 100% ethanol. This data is shown in, FIGS. 15 and 16.

Part C—Effect of Water

The amount of water used in combination with the methanol, ethanol, isopropanol, and acetone also had variable effects on the efficacy of the extraction of the cocoa procyanidins depending on the organic solvent used.

Isopropanol

There was a pronounced decline in procyanidin extraction with increase in oligomeric size for all isopropanol (IPA) dilutions. However, 80% IPA was the least effective aqueous solvent. The 50, 60 & 70% aqueous IPAs were the most effective for all oligomers apart from the decamers, for which 100% IPA was the most effective. It should be noted that for the monomer and lower oligomers (up to the pentamer), the 50-70% IPAs were more than twice as effective as the 80 and 100% IPAs. The data are shown in FIGS. 9 and 10.

Methanol and Ethanol

The data in FIGS. 11, 12, 15, and 16 show that when methanol or ethanol was used, the 70 and 80% aqueous solvents gave the best extractions of lower oligomers, while 100% methanol and ethanol were the most effective for the higher oligomers. For oligomers higher than the pentamer, the lower concentrations of solvent became less effective with increasing oligomeric size, while the 100% methanol and ethanol were more effective.

Acetone

The extraction efficiency of the lower solvent concentrations (50 and 60%) increased with oligomeric size, while the extraction efficiency of the higher solvent concentrations (80 and 100%) decreased with oligomeric size. The data are shown in FIGS. 13 and 14.

One stilled in the art will recognize that the choice of whether to use 100% of solvent or an aqueous-solvent mixture will depend on the oligomeric profile of the procyanidins desired in the cocoa extract.

Part D—The Effect of Temperature

Experiments were carried out to determine the effect of temperature on the extraction of cocoa procyanidins using methanol, ethanol, isopropanol, and acetone. The extractions were carried out as described above, except that they were carried out at 0° C., 20° C., 50° C. and 70° C. except for methanol which has a boiling point of 64° C. When 100% isopropanol was used as the solvent, the efficiency of extraction of all the procyanidin oligomers increased dramatically as the extraction temperature was increased (see FIG. 1b). When 100% ethanol was used as the solvent, the extraction efficiency for all oligomers increased up to 50° C. (see FIG. 1a). When 100% methanol was used the effect of temperature varied with oligomeric size. For example, the yield of the monomers was unaffected by temperature; the yield of the dimers to the heptamers increased as the temperature was increased from 0° C. to 20° C.; and yield of the higher oligomers (octamers to decamers) increased substantially when the temperature was increased to 20° C., but above 20° C. the yield decreased (see FIG. 1c). The data illustrated in FIGS. 1a, 1b, and 1c are shown in FIGS. 17 and 18.

Example 3

Comparison of Solvent Effectiveness in Extracting the Cocoa Procyanidins

For a general comparison of solvent effectiveness see FIG. 2. For each solvent, the dilution which gave the best overall procyanidin yield was selected. As can be seen, the differences in the yields of the monomers and oligomers up to the hexamers did not vary greatly between the solvents. However, for the higher oligomers it became clear that some solvents were preferentially extracting the lower oligomers, while others were preferentially extracting the higher oligomers. For example, isopropanol was an extremely effective solvent for the monomer and lower oligomers, but its efficacy dropped off dramatically for the higher oligomers. Conversely, ethanol was the least effective solvent for extracting the monomer and lower oligomers, but was highly effective for extract the higher oligomers. Overall, the best solvent mixture for the extraction of the cocoa procyanidins was a mixture of 50% acetone, 49.5% deionized water, and 0.5% acetic acid, and this extraction efficiency increased with oligomeric size in comparison with all other solvent systems tested, including the control system.

Example 4

The Effect of Fermentation and Subsequent Processing of the Cocoa Beans on the Extraction of Cocoa Procyanidins This example studies the effect of fermentation on the procyanidin yield by comparing the differences in procyanidin recovery levels from the following groups of cocoa beans. The first group of cocoa beans were not fermented and were freeze-dried and ground according to the method of Part A of Example 1. The second group of cocoa beans were removed from the pod and left in a pile for a period of time sufficient for fermentation to occur, after which they were processed to cocoa solids using the same method as that used for the unfermented cocoa beans. The amount of time required for normal fermentation to occur varies according to the size of the mass of cocoa pods and the frequency with which the pods are turned. It takes about three days for beans to be lightly fermented, between five and seven days for full fermentation to take place, and beans will be over-fermented after eight days. The third group of cocoa beans were not fermented and were not roasted. Rather, they were removed from the pod, sun-dried, and processed according to the method disclosed in the U.S. Pat. No. 6,015,913 (to Kealey et al.). The process involves heating the cocoa beans only for a time and temperature sufficient to reduce the moisture content and loosen the cocoa shells so that the shells can be separated from the nibs in the winnowing step. The beans were subsequently reduced to a powder by the method of Example 1. The cocoa procyanidins were extracted using the "control" extraction method where the solvent was a mixture of 70% acetone, 29.5% water and 0.5% acetic acid. The amount of each of the procyanidin monomers and oligomers present in each extract was determined using the analytical procedure previously described. As shown in FIG. 3, extracts from fermented beans contained between 75 to 100% less cocoa procyanidins than the extract prepared from unfermented beans. The relative loss of procyanidins increased with oligomeric size. Heating the beans to remove the shells also resulted in extract with reduced cocoa procyanidin levels. The cocoa extract from the heated cocoa beans contained levels of procyanidin oligomers which ranged between 10-50% of those found in the cocoa extract from the unfermented cocoa beans.

The results show that the fermentation and subsequent processing of the cocoa beans have a more dramatic effect on the procyanidin content of the extract than the choice of solvent(s).

The above experiment was repeated using the same groups of beans, but altering the method of extraction by using boiling water as the solvent. As can be seen in FIG. 4, the use of boiling water as the solvent drastically reduced the overall yield of cocoa procyanidins. The loss increased with oligomeric size such that the higher oligomers were not extracted using hot water.

Example 5

This example is a comparative example which repeats the extraction process described in a group of Japanese applications and patents owned by a Meiji Seika Kaisha Ltd., where hot aqueous ethanol is the preferred solvent. See JP 9206026, published Aug. 12, 1997; JP 7274894, published Oct. 24, 1995; JP 9224606, published Sep. 2, 1997. In these publications, it is not disclosed if the beans were fermented and roasted. Presumably, the cocoa beans were prepared by the "traditional" method of fermentation followed by roasting and winnowing. As shown above, fermentation and roasting deplete the available supplies of procyanidins in the cocoa bean.

Experiments were carried out to compare the amount of procyanidins and the oligomeric profile of the extract obtained when an extraction was carried out using (a) fermented, (b) underfermented and (c) unfermented, non-roasted cocoa beans processed according to the procedure of U.S. Pat. No. 6,015,913 (Kealey et al.). Cocoa solids were prepared from the three groups of beans by the methods described in Part A of Example 1. Two extracts were made from each group. The first extract was prepared at 50° C. using the standard solvent mixture of acetone/water/acetic acid (70%/29.5%/0.5%) as the solvent. The second extract was prepared at 80° C. using a mixture of 80% ethanol and 20% water as the solvent. The amount of each oligomer present in the aqueous ethanol extract was reported as a percentage of the amount of oligomer present in the standard acetone/water/acetic acid extract. The results are shown in FIG. 22.

The yield of procyanidins was dramatically reduced when the extraction was carried out using fermented beans. Furthermore, there were virtually no higher oligomers in the extract from the fermented beans. The yield of higher oligomers was highest when the extraction was carried out using the same solvent but using unfermented beans. The use of 100% ethanol as the solvent resulted in extremely high yields of the nonamer and decamer (103% for the nonamer and 110% for the decamer compared to the 100% for the standard solvent). The extraction with 80% ethanol gave much lower yields (37% for the nonamer, 18% for the decamer) compared to 100% for the standard solvent.

Example 6

Extraction of Cocoa Procyanidins from Cocoa Powder Using a Counter-Current Extraction Method In a continuous counter-current extraction process, an organic solvent or an aqueous organic solvent passes through an extraction system comprising a plurality of cells containing the partially defatted cocoa solids. The organic solvent or aqueous-organic solvent mixture enters the extraction system at a cell containing the most extracted batch of cocoa solids, passes through progressively fresher batches of cocoa powder contained in successive cells, and is finally drawn off from the cell containing the freshest batch of cocoa solids. Thus, the solvent and the solid to be extracted are moving through the extraction system counter-current to one another. The temperature of the solvent mixture entering the cell containing the most extracted cocoa material may be from about 20° C. to about 100° C., preferably from 50° C. to 95° C. at atmospheric pressure, or higher if the extraction takes place under pressure. The solvent should be in the liquid, as opposed to the gaseous phase, therefore the reaction temperature must either be below the boiling point of the solvent or the reaction must be carried out in a pressurized vessel. Since experimental data generated in the batch processes suggests that the extraction process is more effective at higher temperatures, it may be preferable to carry out the counter current extraction at a higher pressure. The number of cells and cycle time are chosen to give the maximum yields of extracted procyanidins from the cocoa solids. The procyanidin content of the extract is concentrated by recycling the extract in the continuous counter-current system. In such a system the extract passes continuously through the columns in series Periodically, the cell containing the most extracted cocoa solids is removed from the system and one containing fresh cocoa solids is added. The optimum number of cells in series which are used, and the length of each cycle, will vary with particle size of the cocoa solids and extraction parameters such as temperature and pressure. Methods of determining the optimum conditions are well known to those skilled in the art. See "Unit Operations of Chemical Engineering" $3^{rd}$ Edition, Chapter 7, Eds. McCabe, W., and Smith J., McGraw Hill, incorporated herein by reference.

Example 7

Selective Extraction of Procyanidin Oligomers According to their Size

This example demonstrates how extracts containing predominantly high molecular weight cocoa procyanidin oligomers or predominantly low molecular weight oligomers can be obtained by the selective use of solvents which preferentially solubilize certain oligomers.

Figure 7:
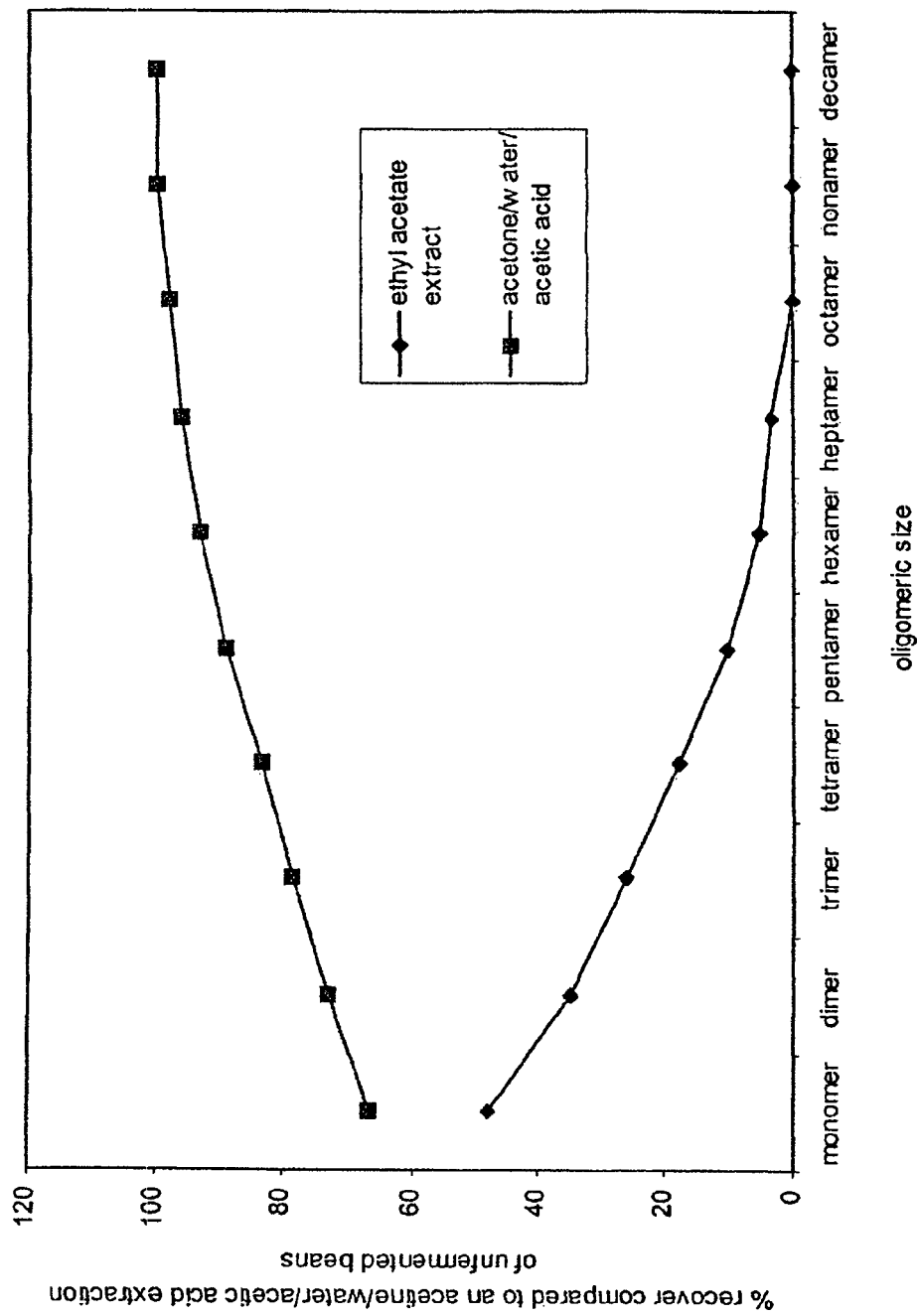
FIG. 7 A graph comparing the oligomeric profiles of an ethyl acetate extraction of cocoa solids, and an acetone/water/acetic acid extract of the ethyl acetate-extracted solids FIG. 8 A graph comparing the oligomeric yield obtained from extractions of fermented and underfermented cocoa solids using 80% aqueous ethanol as the solvent.
Figure 8:
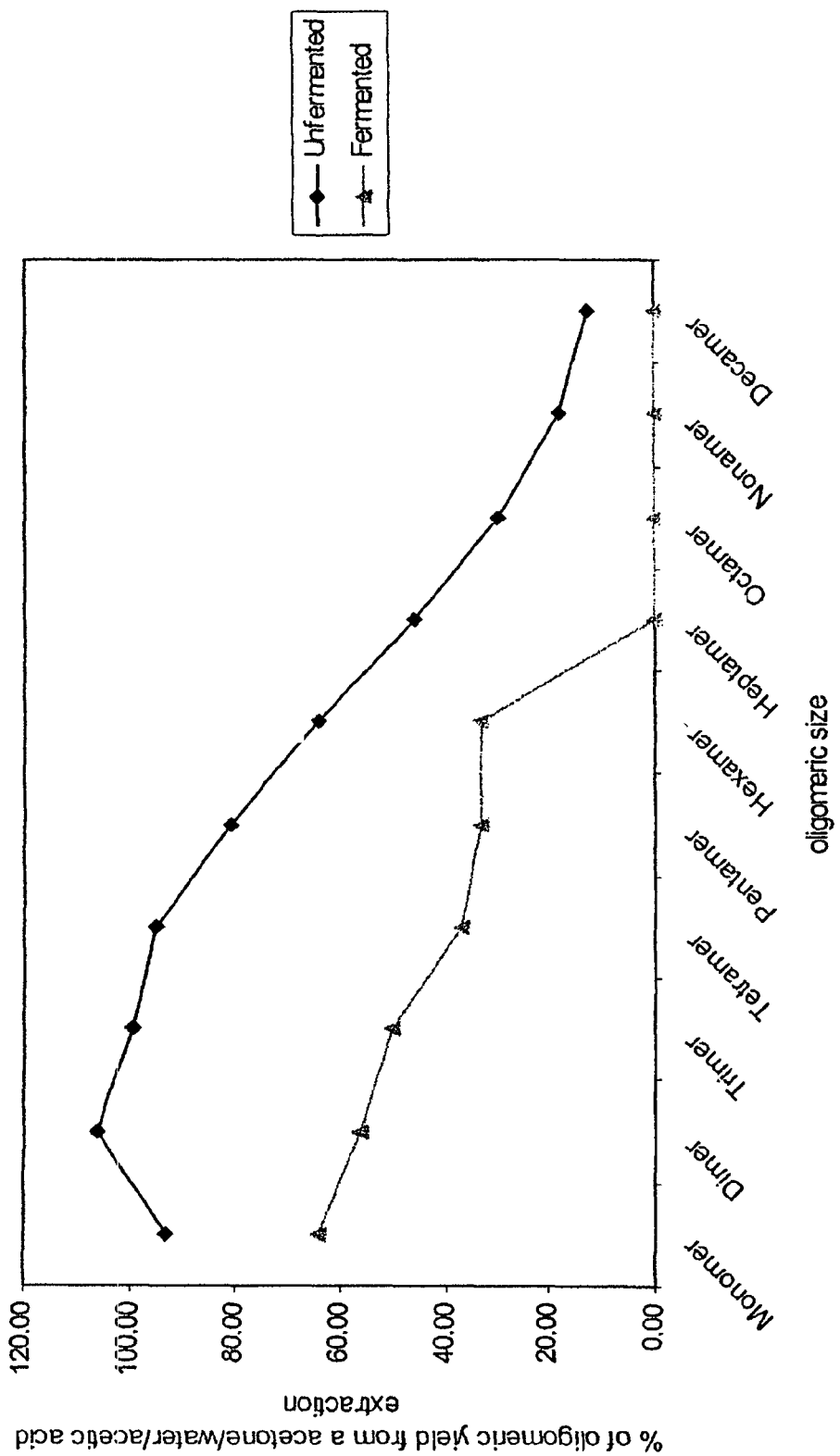

One gram of cocoa powder, obtained from unfermented cocoa beans by the methods described in Example 1, was extracted three times with 100% ethyl acetate at 50° C. The extracts were combined and concentrated by rotary evaporation under vacuum until dry. The dry extract was reconstituted with 10 mls of the standard acetone/water/acetic acid (70%/29.5%/0.5%) solvent and purified and analyzed for oligomeric content as described previously. The ethyl acetate-extracted cocoa solids were then dried in a vacuum oven overnight to remove any residual solvent The dried solids were extracted with the standards acetone/water/acetic acid solvent (70%/29.5%/0.5%) at 50° C., purified, and then analyzed for oligomeric content as described previously. The oligomeric content of both extracts was determined as a percentage of the oligomeric content of an extract prepared from unfermented cocoa beans using the standard acetone/water/acetic acid solvent (70%/29.5%/0.5%) at 50° C. As can be seen in FIG. 7, the use of ethyl acetate as the solvent resulted in the extraction of only the monomer and lower oligomers, leaving all the higher oligomers in the extracted cocoa solids. The higher oligomers were then efficiently extracted using the standard acetone/water/acetic acid solvent (70%/29.5%/0.5%) or 100% ethanol.

Example 8

Detheobromination of the Cocoa Extract

In these experiments, various solvents were used at a range of temperatures to extract cocoa procyanidins from cocoa solids. The extracts were then analyzed to quantify the amount of caffeine and theobromine present in the cocoa extracts. The solvents used were isopropanol, ethanol and methanol. The extractions were carried out at 0°, 20°, 50° and 70° C. using the method described in Example 1.

The results are shown in Table 13. The yields of theobromine were the greatest when ethanol was used as the solvent and the least when isopropanol was used as the solvent. The yields increased with increased temperature. Thus, the results show that theobromine is most soluble in ethanol and least soluble in isopropanol, and that solubility increases with temperature.

To achieve minimum theobromine extraction, and therefore facilitate its removal, the optimum extraction will be extraction with isopropanol carried out at the lowest temperature which results in the extraction of the procyanidins. The theobromine will then be precipitated out of the extract by chilling the extract overnight at about 0°-4° C. and removed by filtering the extract.

To recover the theobromine from cocoa beans, the ideal extraction will be with ethanol at between 50°-70° C. Subsequent to the extraction, the ethanol extract will be chilled to between 0-5° C., which should result in the precipitation of the theobromine. The theobromine is separated by filtration, by centrifugation in a contiguous centrifuge, or by adsorption onto a neutral adsorbent followed by elution.

Preferably, the theobromine is collected as a crude solid by passing the theobromine-laden solvent vapor through a system of chilled plates within closed cabinets (as shown schematically in FIG. 6). The solvent is then be purged from the system and recovered for further use. Meanwhile, the crude theobromine is scraped of the chilled plates, and dissolved in an aqueous solution. Purified, pharmaceutical grade theobromine is obtained by recrystallizing the theobromine, drying the crystals, and redissolving them in de-ionized double-distilled water.

Alternatively, the methylxanthines can be removed from the extract using gel permeation chromatography, as described in U.S. Pat. No. 5,554,646 (issued to Romanczyk et al., Sep. 10, 1996). Briefly, the partial purification process was carried out using liquid chromatography on Sephadex LH 20(28×2.5 cm). Separations were aided by a step gradient into deionized water. The initial gradient composition started with 15% methanol in deionized water, which was followed step-wise every 30 minutes with 25% methanol in deionized water, 35% methanol in deionized water, 70% methanol in deionized water, and finally 100% methanol. The effluent following the elution of caffeine and theobromine was collected as a single fraction, which represents a xanthine alkaloid free sub-fraction of the original extract.

The methylxanthines can also be removed from the cocoa extract by adsorbing them onto a solid adsorbent, after which the extract, substantially free of caffeine and theobromine, is washed through the adsorbent. Various solid adsorbents can be used in the process, such as polymeric resins and activated carbon. Preferably, the adsorbent is substantially neutral in water: and example of a neutral resin adsorbent is semi-calcinated resin XE-340, manufactured by Rohm & Haas; neutral activated carbon can be obtained by either by acid washing of thermally activated carbon followed by rinsing with water to neutrality, or by neutralization of acid-activated carbon with an aqueous alkali followed by rinsing with water to neutrality.

What is claimed is:
1. A process for selectively extracting catechin, epicatechin, and procyanidin dimers and trimers thereof from partially or fully defatted cocoa solids, prepared from cocoa beans that have been dehulled but have not been roasted, which process comprises the step of extracting the cocoa solids with methyl acetate or ethyl acetate.

2. The process of claim 1, wherein the extracting is carried out at about 20° C. to about 50° C.

3. The process of claim 1, wherein the cocoa beans have a fermentation factor of 275 or less.

4. The process of claim 1, wherein the cocoa beans are slaty, purple, or purple brown cocoa beans or mixtures of slaty and purple cocoa beans, purple and brown cocoa beans, or slaty, purple, and brown cocoa beans.

5. The process of claim 4, wherein the extraction is carried out at about 20° C. to about 50° C.

6. The process of claim 4, wherein the extraction is carried out with ethyl acetate at about 50° C.

* * * * *